US008877199B2

(12) United States Patent
Rader et al.

(10) Patent No.: US 8,877,199 B2
(45) Date of Patent: Nov. 4, 2014

(54) B CELL SURFACE REACTIVE ANTIBODIES

(75) Inventors: Christoph Rader, Olney, MD (US); Sivasubramanian Baskar, Elicott City, MD (US); Michael R. Bishop, Williams Bay, WI (US); Ivan Samija, Zagreb (HR); Jessica M. Suschak, Jefferson, MA (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 16 days.

(21) Appl. No.: 13/320,630

(22) PCT Filed: May 12, 2010

(86) PCT No.: PCT/US2010/034491
§ 371 (c)(1),
(2), (4) Date: Feb. 1, 2012

(87) PCT Pub. No.: WO2010/132532
PCT Pub. Date: Nov. 18, 2010

(65) Prior Publication Data
US 2012/0121504 A1 May 17, 2012

Related U.S. Application Data

(60) Provisional application No. 61/178,688, filed on May 15, 2009.

(51) Int. Cl.
*A61K 39/395* (2006.01)
*C07K 16/30* (2006.01)
*A61K 51/10* (2006.01)
*C07K 16/00* (2006.01)
*G01N 33/574* (2006.01)
*G01N 33/569* (2006.01)

(52) U.S. Cl.
CPC ....... *C07K 16/3061* (2013.01); *C07K 2317/565* (2013.01); *C07K 2317/55* (2013.01); *C07K 2317/21* (2013.01); *C07K 16/005* (2013.01); *C07K 2317/56* (2013.01); *G01N 33/57426* (2013.01); *G01N 33/56972* (2013.01)
USPC .................. 424/155.1; 424/142.1; 424/135.1; 424/136.1; 424/178.1; 530/387.3; 530/388.15; 530/388.8; 530/391.3; 530/391.7

(58) Field of Classification Search
None
See application file for complete search history.

(56) References Cited

U.S. PATENT DOCUMENTS

| | | | |
|---|---|---|---|
| 3,832,253 A | 8/1974 | Di Palma et al. | |
| 3,854,480 A | 12/1974 | Zaffaroni | |
| 4,452,775 A | 6/1984 | Kent | |
| 4,667,014 A | 5/1987 | Nestor et al. | |
| 4,748,034 A | 5/1988 | de Rham | |
| 5,075,109 A | 12/1991 | Tice et al. | |
| 5,843,749 A | 12/1998 | Maisonpierre et al. | |
| 6,129,914 A | 10/2000 | Weiner et al. | |
| 2003/0232009 A1 | 12/2003 | Babcook et al. | |
| 2004/0018198 A1 | 1/2004 | Gudas et al. | |
| 2004/0265960 A1 | 12/2004 | Valge-Archer et al. | |
| 2005/0059113 A1 | 3/2005 | Bedian et al. | |
| 2006/0257398 A1 | 11/2006 | Hansen et al. | |
| 2007/0004910 A1 | 1/2007 | Sexton et al. | |
| 2007/0072177 A1 | 3/2007 | Bakker et al. | |
| 2007/0179086 A1 | 8/2007 | Gliniak et al. | |
| 2007/0207510 A1 | 9/2007 | Kipps et al. | |
| 2008/0299136 A1 | 12/2008 | Ernst et al. | |

FOREIGN PATENT DOCUMENTS

| | | | |
|---|---|---|---|
| WO | WO2004/067569 | * | 8/2004 |
| WO | WO 2004/067569 A1 | | 8/2004 |
| WO | WO 2004/110369 A2 | | 12/2004 |
| WO | WO 2005/030124 A2 | | 4/2005 |
| WO | WO 2005/100605 A1 | | 10/2005 |
| WO | WO 2007/141278 A2 | | 12/2007 |
| WO | WO 2008/074004 A2 | | 6/2008 |
| WO | WO 2008/103849 A2 | | 8/2008 |
| WO | WO 2008/122039 A2 | | 10/2008 |
| WO | WO 2009/018411 A1 | | 2/2009 |
| WO | WO 2010/017103 A2 | | 2/2010 |

OTHER PUBLICATIONS

Johnson and Wu, Antibiody Engineering: Methods and Protocols, vol. 248, p. 11-25, 2004.*
Bendig, Methods: A Companion to Methods in Enzymology, vol. 8, p. 83-93, 1995.*
Colman, Research in Immunology, vol. 145, p. 33-36, 1994.*
MacCallum, Journal of Molecular Biology, vol. 262, p. 732-745, 1996.*
Paul, Fundamental Immunology, Third Edition, p. 292-295, 1993.*
Rudikoff, Proceedings of the National Academy of Sciences, U.S.A., vol. 79, p. 1979-1983, 1982.*
Panka, Proceedings of the National Academy of Sciences, U.S.A., vol. 85, p. 3080-3084, 1988.*
Schmiedl, Protein Engineering, vol. 13, No. 10, p. 725-734, 2000.*
Casset, Biochemical and Biophysical Research Communications, vol. 307, p. 198-205, 2003.*
Aman et al., "Epstein-Barr virus susceptibility of normal human B lymphocyte populations," *J. Exp. Med.*, 159 (1), 208-220 (1984).
Baskar et al., "A Human Monoclonal Antibody and Target Discovery Platform Based on Allogeneic Hematopoietic Stem Cell Transplantation and Phage Display" presented at the Keystone Symposium "Antibodies as Drugs: From Basic Biology to the Clinic," Lake Louise, Alberta, Canada, Feb. 1-6, 2007.

(Continued)

*Primary Examiner* — Misook Yu
*Assistant Examiner* — Michael D Allen
(74) *Attorney, Agent, or Firm* — Leydig, Voit & Mayer, Ltd.

(57) ABSTRACT

The invention relates to antibodies that are reactive to the cell surface of CD19+ B cells, including B-cell chronic lymphocytic leukemia (B-CLL) cells, and compositions and methods for using such antibodies, including in the diagnosis and treatment of disorders associated with CD19+ B cells, such as B-CLL.

17 Claims, 9 Drawing Sheets

(56) References Cited

OTHER PUBLICATIONS

Baskar et al., "A Human Monoclonal Antibody and Antigen Discovery Platform Based on Allogeneic Hematopoietic Stem Cell Transplantation and Phage Display" presented at the National Cancer Institute meeting "Cancer Immunology and Immunotherapy: Realizing the Promise," Bethesda, MD, Sep. 11-12, 2008.

Baskar et al., "A human monoclonal antibody drug and target discovery platform for B-cell chronic lymphocytic leukemia based on allogeneic hematopoietic stem cell transplantation and phage display," *Blood*, 114 (20), 4494-4502 (2009).

Bleakley et al., "Molecules and mechanisms of the graft-versus-leukaemia effect," *Nat. Rev. Cancer*, 4 (5), 371-380 (2004).

Boyiadzis et al., "Hematopoietic stem cell transplantation for chronic lymphocytic leukemia: potential cure for an incurable disease," *Expert Opin. Biol. Ther.*, 7 (12), 1789-1797 (2007).

Byrd, "Hunting for the Achilles' heel of CLL," *Blood*, 114 (20), 4324 (2009).

Eshhar, "The T-body approach: redirecting T cells with antibody specificity," in *Therapeutic Antibodies: Handbook of Experimental Pharmacology 181*, Chernajovsky et al., eds., pp. 329-342, Springer-Verlag, Berlin (2008).

European Patent Office, International Search Report in International Patent Application PCT/US2010/034491 (Oct. 1, 2010).

European Patent Office, Written Opinion in International Patent Application PCT/US2010/034491 (Oct. 1, 2010).

Gribben, "Stem cell transplantation in chronic lymphocytic leukemia," *Biol. Blood Marrow Transplant*, 15 (1 Suppl.), 53-58 (2008).

Hambach et al., "Immunotherapy of cancer through targeting of minor histocompatibility antigens," *Curr. Opin Immunol.*, 17 (2), 202-210 (2005).

Hofer et al., "Chimeric rabbit/human Fab and IgG specific for members of the Nogo-66 receptor family selected for species cross-reactivity with an improved phage display vector," *J. Immunol. Methods*, 318 (1-2), 75-87 (2007).

Klein et al., "Gene expression profiling of B cell chronic lymphocytic leukemia reveals a homogeneous phenotype related to memory B cells," *J. Exp. Med.*, 194 (11), 1625-1638 (2001).

Kolb, "Graft-versus-leukemia effects of transplantation and donor lymphocytes," *Blood*, 112 (12), 4371-4383 (2008).

Krackhardt et al., "Identification of tumor-associated antigens in chronic lymphocytic leukemia by SEREX," *Blood*, 100 (6), 2123-2131 (2002).

Kwong et al., "Generation, affinity maturation, and characterization of a human anti-human NKG2D monoclonal antibody with dual antagonistic and agonistic activity," *J. Mol. Biol.*, 384 (5), 1143-1156 (2008).

Marcu-Malina et al., "Re-targeting T-cells against cancer by gene-transfer of tumor-reactive receptors," *Exp. Opin. Biol. Ther.*, 9 (5), 579-591 (2009).

Popkov et al., "Rabbit immune repertoires as sources for therapeutic monoclonal antibodies: the impact of kappa allotype-correlated variation in cysteine content on antibody libraries selected by phage display," *J. Mol. Biol.*, 325 (2), 325-335 (2003).

Proto-Siqueira et al., "SAGE analysis demonstrates increased expression of TOSO contributing to FAS-mediated resistance in CLL," *Blood*, 112 (2), 394-397 (2008).

Rader et al., "Integrin $\alpha(v)\beta 3$ targeted therapy for Kaposi's sarcoma with an in vitro evolved antibody," *FASEB J.*, 16 (14), 2000-2002.

Rader et al., "Generation and selection of rabbit antibody libraries by phage display," in *Methods in Molecular. Biology: Therapeutic Antibodies*, Dimitrov, ed., pp. 101-128, Humana Press, New York (2009).

Rosenwald et al., "Relation of gene expression phenotype to immunoglobulin mutation genotype in B cell chronic lymphocytic leukemia," *J. Exp. Med.*, 194 (11), 1639-1647 (2001).

Russell et al., "Structural features can be unconserved in proteins with similar folds. An analysis of side-chain to side-chain contacts secondary structure and accessibility," *J. Mol. Biol.*, 244 (3), 332-350 (1994).

Saltman et al., "Establishment of a karyotypically normal B-chronic lymphocytic leukemia cell line; evidence of leukemic origin by immunoglobulin gene rearrangement," *Leuk. Res.*, 14 (4), 381-387 (1990).

Stamatopoulos et al., "Immunoglobulin light chain repertoire in chronic lymphocytic leukemia," *Blood*, 106 (10), 3575-3583 (2005).

Wendel-Hansen et al., "Epstein-Barr virus (EBV) can immortalize B-cll cells activated by cytokines," *Leukemia*, 8 (3), 476-484 (1994).

Wu et al., "Arming antibodies: prospects and challenges for immunoconjugates," *Nat. Biotechnol.*, 23 (9), 1137-1146 (2005).

Wu et al., "Induction of tumor immunity following allogeneic stem cell transplantation," in *Advanced Immunology 90*, Allison et al., eds., pp. 133-173, Elsevier Academic Press, San Diego (2006).

International Bureau of WIPO, International Preliminary Report on Patentability, issued in PCT/US2010/034491, mailed Nov. 24, 2011 (13 pages).

\* cited by examiner

AMINO ACID SEQUENCES OF K-LIGHT CHAIN VARIABLE DOMAINS
(underlined residues differ from JML-1)

JML-1: DIQMTQSPSSLSASVGDRVTITCRASQSISSYLNWYQQKPGKAPKLLIYAASSLQSGVPSRFSGSGSGTDFTLTISSLQPEDFATYYCQQSYSTPFTFGPGTKVDIK (SEQ ID NO:1)

- FR1     DIQMTQSPSSLSASVGDRVTITC (SEQ ID NO:2)
- CDR1   RASQSISSYLN (SEQ ID NO:3)
- FR2     WYQQKPGKAPKLLIY (SEQ ID NO:4)
- CDR2   AASSLQS (SEQ ID NO:5)
- FR3     GVPSRFSGSGSGTDFTLTISSLQPEDFATYYC (SEQ ID NO:6)
- CDR3   QQSYSTPFT (SEQ ID NO:7)
- FR4     FGPGTKVDIK (SEQ ID NO:8)

JML-3: DI<u>V</u>MTQSPSSLSASVGDRVTITCRASQSISSYLNWYQQKPGKAPKLLIYAASSLQSG<u>I</u>PSRFSGSGSGTDFTLTISSLQPEDFATYYCQQSYSTPFTFGPGTKVDIK (SEQ ID NO:9)

- FR1     DI<u>V</u>MTQSPSSLSASVGDRVTITC (SEQ ID NO:10)
- CDR1   RASQSISSYLN (SEQ ID NO:3)
- FR2     WYQQKPGKAPKLLIY (SEQ ID NO:4)
- CDR2   AASSLQS (SEQ ID NO:5)
- FR3     G<u>I</u>PSRFSGSGSGTDFTLTISSLQPEDFATYYC (SEQ ID NO:11)
- CDR3   QQSYSTPFT (SEQ ID NO:7)
- FR4     FGPGTKVDIK (SEQ ID NO:8)

JML-7: DIQ<u>L</u>TQSPSSLSASVGDRVTITCRASQSISSYLNWYQQKPGKAPKLLIYAASSLQSGVPSRFSGSGSGTDFTLTISSLQPEDFATYYCQQSYSTPFTFGPGTKVDIK (SEQ ID NO:12)

- FR1     DIQ<u>L</u>TQSPSSLSASVGDRVTITC (SEQ ID NO:13)
- CDR1   RASQSISSYLN (SEQ ID NO:3)
- FR2     WYQQKPGKAPKLLIY (SEQ ID NO:4)
- CDR2   AASSLQS (SEQ ID NO:5)
- FR3     GVPSRFSGSGSGTDFTLTISSLQPEDFATYYC (SEQ ID NO:6)
- CDR3   QQSYSTPFT (SEQ ID NO:7)
- FR4     FGPGTKVDIK (SEQ ID NO:8)

JML-13: DIQMTQSPS<u>T</u>LSASVGDRVTITCRASQSISSYLNWYQQKPGKAPKLLIY<u>GA</u>SSLQSGVPSRFSGSGSGTDFTLTISSLQPEDFATYYCQQSYSTPFTFGPGTKVDIK (SEQ ID NO:14)

- FR1     DIQMTQSPS<u>T</u>LSASVGDRVTITC (SEQ ID NO:15)
- CDR1   RASQSISSYLN (SEQ ID NO:3)
- FR2     WYQQKPGKAPKLLIY (SEQ ID NO:4)
- CDR2   <u>G</u>ASSLQS (SEQ ID NO:16)
- FR3     GVPSRFSGSGSGTDFTLT<u>I</u>TSLQPEDFATYYC (SEQ ID NO:17)
- CDR3   QQSYSTPFT (SEQ ID NO:7)
- FR4     FGPGTKVDIK (SEQ ID NO:8)

Figure 7

AMINO ACID SEQUENCES OF HEAVY CHAIN VARIABLE DOMAINS
(underlined residues differ from JML-1)

JML-1: KVQLLESGGGLVQPGRSLRLSCAASGFTFDDYGMHWVRQAPGKGLEWV
SGISWNSGSIGYADSVKGRFTISRDNSKNTLYLQMNSLRAEDTAVYYCARGGQTIDI
WGQGTMVTVSS (SEQ ID NO:18)

FR1     KVQLLESGGGLVQPGRSLRLSCAASGFTFD (SEQ ID NO:19)
    CDR1   DYGMH (SEQ ID NO:20)
    FR2     WVRQAPGKGLEWVS (SEQ ID NO:21)
    CDR2   GISWNSGSIGYADSVKG (SEQ ID NO:22)
    FR3     RFTISRDNSKNTLYLQMNSLRAEDTAVYYCAR (SEQ ID NO:23)
    CDR3   GGQTIDI (SEQ ID NO:24)
    FR4     WGQGTMVTVSS (SEQ ID NO:25)

JML-3: EVQLLESGGGLVQPGRSLRLSCAASGFTFSSYGMHWVRQAPGKGLEWV
AVISYDGSNKYYADSVKGRFTISRDNSKNTLYLQMNSLRAEDTAVYYCARGGQTIDI
WGQGTMVTVSS (SEQ ID NO:26)

FR1     EVQLLESGGGVVQPGRSLRLSCAASGFTFS (SEQ ID NO:27)
    CDR1   SYGMH (SEQ ID NO:28)
    FR2     WVRQAPGKGLEWVA (SEQ ID NO:29)
    CDR2   VISYDGSNKYYADSVKG (SEQ ID NO:30)
    FR3     RFTISRDNSKNTLYLQMNSLRAEDTAVYYCAR (SEQ ID NO:23)
    CDR3   GGQTIDI (SEQ ID NO:24)
    FR4     WGQGTMVTVSS (SEQ ID NO:25)

JML-7: KVQLLESGGGVVQPGRSLRLSCAASGFTFSSYGMHWVRQAPGKGLEWV
AVISYDGSNKYYADSVKGRFTISRDNSKNTLYLQMNSLRAEDTAVYYCARGGQTIDI
WGQGTMVTVSS (SEQ ID NO:31)

FR1     KVQLLESGGGVVQPGRSLRLSCAASGFTFS (SEQ ID NO:32)
    CDR1   SYGMH (SEQ ID NO:28)
    FR2     WVRQAPGKGLEWVA (SEQ ID NO:29)
    CDR2   VISYDGSNKYYADSVKG (SEQ ID NO:30)
    FR3     RFTISRDNSKNTLYLQMNSLRAEDTAVYYCAR (SEQ ID NO:23)
    CDR3   GGQTIDI (SEQ ID NO:24)
    FR4     WGQGTMVTVSS (SEQ ID NO:25)

JML-13: EVQLVESGGGVVQPGRSLRLSCAASGFTFSSYGMHWVRQAPGKGLEW
VAVISYDGSNKYYADSVKGRFTISRDNSKNTLYLQMNSLRAEDTAVYYCARGGQTI
DIWGQGTMVTVSS (SEQ ID NO:33)

FR1     EVQLVESGGGVVQPGRSLRLSCAASGFTFS (SEQ ID NO:34)
    CDR1   SYGMH (SEQ ID NO:28)
    FR2     WVRQAPGKGLEWVA (SEQ ID NO:29)
    CDR2   VISYDGSNKYYADSVKG (SEQ ID NO:30)
    FR3     RFTISRDNSKNTLYLQMNSLRAEDTAVYYCAR (SEQ ID NO:23)
    CDR3   GGQTIDI (SEQ ID NO:24)
    FR4     WGQGTMVTVSS (SEQ ID NO:25)

Figure 8

SEQUENCE LISTING

<160> NUMBER OF SEQ ID NOS: 34

<210> SEQ ID NO 1
<211> LENGTH: 107
<212> TYPE: PRT
<213> ORGANISM: Artificial Sequence
<220> FEATURE:
<223> OTHER INFORMATION: Source: phage library of human antibody
      sequences

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 2
<211> LENGTH: 23
<212> TYPE: PRT
<213> ORGANISM: Artificial Sequence
<220> FEATURE:
<223> OTHER INFORMATION: Source: phage library of human antibody
      sequences

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 3
<211> LENGTH: 11
<212> TYPE: PRT
<213> ORGANISM: Artificial Sequence
<220> FEATURE:
<223> OTHER INFORMATION: Source: phage library of human antibody
      sequences

<400> SEQUENCE: 3

Arg Ala Ser Gln Ser Ile Ser Ser Tyr Leu Asn
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Source: phage library of human antibody
      sequences

<400> SEQUENCE: 4

Trp Tyr Gln Gln Lys Pro Gly Lys Ala Pro Lys Leu Leu Ile Tyr
1               5                   10                  15

```
<210> SEQ ID NO 5
<211> LENGTH: 7
<212> TYPE: PRT
<213> ORGANISM: Artificial Sequence
<220> FEATURE:
<223> OTHER INFORMATION: Source: phage library of human antibody
      sequences

<400> SEQUENCE: 5

Ala Ala Ser Ser Leu Gln Ser
1               5

<210> SEQ ID NO 6
<211> LENGTH: 32
<212> TYPE: PRT
<213> ORGANISM: Artificial Sequence
<220> FEATURE:
<223> OTHER INFORMATION: Source: phage library of human antibody
      sequences

<400> SEQUENCE: 6

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 7
<211> LENGTH: 9
<212> TYPE: PRT
<213> ORGANISM: Artificial Sequence
<220> FEATURE:
<223> OTHER INFORMATION: Source: phage library of human antibody
      sequences

<400> SEQUENCE: 7

Gln Gln Ser Tyr Ser Thr Pro Phe Thr
1               5

<210> SEQ ID NO 8
<211> LENGTH: 10
<212> TYPE: PRT
<213> ORGANISM: Artificial Sequence
<220> FEATURE:
<223> OTHER INFORMATION: Source: phage library of human antibody
      sequences

<400> SEQUENCE: 8

Phe Gly Pro Gly Thr Lys Val Asp Ile Lys
1               5                   10

<210> SEQ ID NO 9
<211> LENGTH: 107
<212> TYPE: PRT
<213> ORGANISM: Artificial Sequence
<220> FEATURE:
<223> OTHER INFORMATION: Source: phage library of human antibody
      sequences

<400> SEQUENCE: 9

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Phe
                 85                  90                  95

Thr Phe Gly Pro Gly Thr Lys Val Asp Ile Lys
                100                 105

<210> SEQ ID NO 10
<211> LENGTH: 23
<212> TYPE: PRT
<213> ORGANISM: Artificial Sequence
<220> FEATURE:
<223> OTHER INFORMATION: Source: phage library of human antibody
      sequences

<400> SEQUENCE: 10

Asp Ile Val Met Thr Gln Ser Pro Ser Ser Leu Ser Ala Ser Val Gly
 1               5                  10                  15

Asp Arg Val Thr Ile Thr Cys
                 20

<210> SEQ ID NO 11
<211> LENGTH: 32
<212> TYPE: PRT
<213> ORGANISM: Artificial Sequence
<220> FEATURE:
<223> OTHER INFORMATION: Source: phage library of human antibody
      sequences

<400> SEQUENCE: 11

Gly Ile Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
                 20                  25                  30

<210> SEQ ID NO 12
<211> LENGTH: 107
<212> TYPE: PRT
<213> ORGANISM: Artificial Sequence
<220> FEATURE:
<223> OTHER INFORMATION: Source: phage library of human antibody
      sequences

<400> SEQUENCE: 12

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
                 35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Phe
                 85                  90                  95

Thr Phe Gly Pro Gly Thr Lys Val Asp Ile Lys
                100                 105
```

```
<210> SEQ ID NO 13
<211> LENGTH: 23
<212> TYPE: PRT
<213> ORGANISM: Artificial Sequence
<220> FEATURE:
<223> OTHER INFORMATION: Source: phage library of human antibody
      sequences

<400> SEQUENCE: 13

Asp Ile Gln Leu Thr Gln Ser Pro Ser Leu Ser Ala Ser Val Gly
1               5                  10                  15

Asp Arg Val Thr Ile Thr Cys
            20

<210> SEQ ID NO 14
<211> LENGTH: 107
<212> TYPE: PRT
<213> ORGANISM: Artificial Sequence
<220> FEATURE:
<223> OTHER INFORMATION: Source: phage library of human antibody
      sequences

<400> SEQUENCE: 14

Asp Ile Gln Met Thr Gln Ser Pro Ser Thr Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 15
<211> LENGTH: 23
<212> TYPE: PRT
<213> ORGANISM: Artificial Sequence
<220> FEATURE:
<223> OTHER INFORMATION: Source: phage library of human antibody
      sequences

<400> SEQUENCE: 15

Asp Ile Gln Met Thr Gln Ser Pro Ser Thr Leu Ser Ala Ser Val Gly
1               5                  10                  15

Asp Arg Val Thr Ile Thr Cys
            20

<210> SEQ ID NO 16
<211> LENGTH: 7
<212> TYPE: PRT
<213> ORGANISM: Artificial Sequence
<220> FEATURE:
<223> OTHER INFORMATION: Source: phage library of human antibody
      sequences

<400> SEQUENCE: 16

Gly Ala Ser Ser Leu Gln Ser
1               5
```

```
<210> SEQ ID NO 17
<211> LENGTH: 32
<212> TYPE: PRT
<213> ORGANISM: Artificial Sequence
<220> FEATURE:
<223> OTHER INFORMATION: Source: phage library of human antibody
      sequences

<400> SEQUENCE: 17

Gly Val Pro Ser Arg Phe Ser Gly Ser Gly Ser Gly Thr Asp Phe Thr
1               5                   10                  15

Leu Thr Ile Thr Ser Leu Gln Pro Glu Asp Phe Ala Thr Tyr Tyr Cys
            20                  25                  30

<210> SEQ ID NO 18
<211> LENGTH: 116
<212> TYPE: PRT
<213> ORGANISM: Artificial Sequence
<220> FEATURE:
<223> OTHER INFORMATION: Source: phage library of human antibody
      sequences

<400> SEQUENCE: 18

Lys Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Gly Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Thr Ile Asp Ile Trp Gly Gln Gly Thr Met Val
            100                 105                 110

Thr Val Ser Ser
        115

<210> SEQ ID NO 19
<211> LENGTH: 30
<212> TYPE: PRT
<213> ORGANISM: Artificial Sequence
<220> FEATURE:
<223> OTHER INFORMATION: Source: phage library of human antibody
      sequences

<400> SEQUENCE: 19

Lys Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp
            20                  25                  30

<210> SEQ ID NO 20
<211> LENGTH: 5
<212> TYPE: PRT
<213> ORGANISM: Artificial Sequence
<220> FEATURE:
<223> OTHER INFORMATION: Source: phage library of human antibody
      sequences
```

```
<400> SEQUENCE: 20

Asp Tyr Gly Met His
1               5

<210> SEQ ID NO 21
<211> LENGTH: 14
<212> TYPE: PRT
<213> ORGANISM: Artificial Sequence
<220> FEATURE:
<223> OTHER INFORMATION: Source: phage library of human antibody
      sequences

<400> SEQUENCE: 21

Trp Val Arg Gln Ala Pro Gly Lys Gly Leu Glu Trp Val Ser
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Source: phage library of human antibody
      sequences

<400> SEQUENCE: 22

Gly Ile Ser Trp Asn Ser Gly Ser Ile Gly Tyr Ala Asp Ser Val Lys
1               5                   10                  15

Gly

<210> SEQ ID NO 23
<211> LENGTH: 32
<212> TYPE: PRT
<213> ORGANISM: Artificial Sequence
<220> FEATURE:
<223> OTHER INFORMATION: Source: phage library of human antibody
      sequences

<400> SEQUENCE: 23

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 24
<211> LENGTH: 7
<212> TYPE: PRT
<213> ORGANISM: Artificial Sequence
<220> FEATURE:
<223> OTHER INFORMATION: Source: phage library of human antibody
      sequences

<400> SEQUENCE: 24

Gly Gly Gln Thr Ile Asp Ile
1               5

<210> SEQ ID NO 25
<211> LENGTH: 11
<212> TYPE: PRT
<213> ORGANISM: Artificial Sequence
<220> FEATURE:
<223> OTHER INFORMATION: Source: phage library of human antibody
      sequences

<400> SEQUENCE: 25

Trp Gly Gln Gly Thr Met Val Thr Val Ser Ser
1               5                   10
```

```
<210> SEQ ID NO 26
<211> LENGTH: 116
<212> TYPE: PRT
<213> ORGANISM: Artificial Sequence
<220> FEATURE:
<223> OTHER INFORMATION: Source: phage library of human antibody
      sequences

<400> SEQUENCE: 26

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Thr Ile Asp Ile Trp Gly Gln Gly Thr Met Val
            100                 105                 110

Thr Val Ser Ser
        115

<210> SEQ ID NO 27
<211> LENGTH: 30
<212> TYPE: PRT
<213> ORGANISM: Artificial Sequence
<220> FEATURE:
<223> OTHER INFORMATION: Source: phage library of human antibody
      sequences

<400> SEQUENCE: 27

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 28
<211> LENGTH: 5
<212> TYPE: PRT
<213> ORGANISM: Artificial Sequence
<220> FEATURE:
<223> OTHER INFORMATION: Source: phage library of human antibody
      sequences

<400> SEQUENCE: 28

Ser Tyr Gly Met His
1               5

<210> SEQ ID NO 29
<211> LENGTH: 14
<212> TYPE: PRT
<213> ORGANISM: Artificial Sequence
<220> FEATURE:
<223> OTHER INFORMATION: Source: phage library of human antibody
      sequences

<400> SEQUENCE: 29

Trp Val Arg Gln Ala Pro Gly Lys Gly Leu Glu Trp Val Ala
1               5                   10
```

-continued

```
<210> SEQ ID NO 30
<211> LENGTH: 17
<212> TYPE: PRT
<213> ORGANISM: Artificial Sequence
<220> FEATURE:
<223> OTHER INFORMATION: Source: phage library of human antibody
      sequences

<400> SEQUENCE: 30

Val Ile Ser Tyr Asp Gly Ser Asn Lys Tyr Tyr Ala Asp Ser Val Lys
1               5                   10                  15

Gly

<210> SEQ ID NO 31
<211> LENGTH: 116
<212> TYPE: PRT
<213> ORGANISM: Artificial Sequence
<220> FEATURE:
<223> OTHER INFORMATION: Source: phage library of human antibody
      sequences

<400> SEQUENCE: 31

Lys Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Thr Ile Asp Ile Trp Gly Gln Gly Thr Met Val
            100                 105                 110

Thr Val Ser Ser
        115

<210> SEQ ID NO 32
<211> LENGTH: 30
<212> TYPE: PRT
<213> ORGANISM: Artificial Sequence
<220> FEATURE:
<223> OTHER INFORMATION: Source: phage library of human antibody
      sequences

<400> SEQUENCE: 32

Lys Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 33
<211> LENGTH: 116
<212> TYPE: PRT
<213> ORGANISM: Artificial Sequence
<220> FEATURE:
<223> OTHER INFORMATION: Source: phage library of human antibody
      sequences
```

```
<400> SEQUENCE: 33

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Thr Ile Asp Ile Trp Gly Gln Gly Thr Met Val
            100                 105                 110

Thr Val Ser Ser
        115

<210> SEQ ID NO 34
<211> LENGTH: 30
<212> TYPE: PRT
<213> ORGANISM: Artificial Sequence
<220> FEATURE:
<223> OTHER INFORMATION: Source: phage library of human antibody
      sequences

<400> SEQUENCE: 34

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30
```

B CELL SURFACE REACTIVE ANTIBODIES

CROSS-REFERENCE TO RELATED APPLICATIONS

This patent application is a U.S. national phase of International Patent Application No. PCT/US2010/034491, filed May 12, 2010, which claims the benefit of U.S. Provisional Patent Application No. 61/178,688 filed May 15, 2009, the complete contents of which are hereby incorporated by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 17,116 Byte ASCII (Text) file named "709042 ST25.TXT," created on Oct. 11, 2011.

BACKGROUND OF THE INVENTION

Antibody therapies and diagnostics have been developed for use in treating a wide range of conditions including autoimmune diseases or disorders, infectious diseases, and cancers. Such therapies are useful but also can be undesirably immunogenic and damaging to healthy cells and tissues.

About 30% of all diagnosed leukemias are B-cell chronic lymphocytic leukemia (B-CLL), and the incidence of B-CLL is estimated to include 15,000 new cases and 4,500 deaths in the United States alone. Although generally considered incurable, a number of chemotherapies and biological therapies have been clinically tested in B-CLL patients. Of these, allogeneic hematopoietic stem cell transplantation (alloHSCT) may be the only curative treatment for some B-CLL patients. Boyiadzis et al., *Expert Opin. Biol. Ther.*, 7: 1789-1797 (2007) and Gribben, J. G., *Biol. Blood Marrow Transplant*, 15: 53-58 (2008). AlloHSCT is believed to induce a graft-versus-leukemia (GVL) response in alloHSCT recipients. This GVL may be mediated by alloreactive donor T cells and/or donor B cell-derived allo-HSCT-induced antibodies. Bleakley et al., *Nat. Rev. Cancer*, 4: 371-380 (2004), Hambach et al., *Curr. Opin. Immunol.*, 17: 202-210 (2005), and Wu et al., *Adv. Immunol.*, 90: 133-173 (2006). Other clinically tested biological therapies include the use of rituximab and alemtuzumab. These therapeutic antibodies, however, target antigens found on both malignant and normal B cell surfaces. The CD52 antigen targeted by alemtuzumab is also expressed on the cell surface of a variety of other normal immune system cells. Accordingly, immunosupression can be a concern with such antibodies.

Strategies that have been used in attempts to identify antigens specific to malignant B-cells include differential gene expression profiling and SEREX analysis. SEREX involves using serum antibodies from cancer patients to screen recombinant cDNA expression libraries. These strategies, however, do not necessarily distinguish intracellular antigens from cell surface antigens.

There is a desire for additional antibody therapies that preferentially target malignant B cell surface antigens, have good efficacy, and are minimally immunogenic and/or damaging to non-diseased cells.

BRIEF SUMMARY OF THE INVENTION

The invention provides an isolated antibody with specificity for a cell surface marker found on certain CD19+ B cells such as B-CLL. In particular, the invention provides an isolated antibody that has B-CLL cell surface reactivity and includes (a) a light chain variable domain having at least 90% identity to a sequence selected from the group consisting of SEQ ID NO:1, SEQ ID NO:9, SEQ ID NO:12, and SEQ ID NO:14, (b) a heavy chain variable domain having at least 90% identity to a sequence selected from the group consisting of SEQ ID NO:18, SEQ ID NO:26, SEQ ID NO:31, and SEQ ID NO:33, or (c) both a light chain of (a) and a heavy chain of (b).

The invention also provides an isolated antibody that has B-CLL cell surface reactivity and includes at least one complementarity determining region (CDR) having a sequence selected from the group consisting of SEQ ID NO:3, SEQ ID NO:5, SEQ ID NO:7, SEQ ID NO:16, SEQ ID NO:20, SEQ ID NO:22, SEQ ID NO:24, SEQ ID NO:28, and SEQ ID NO:30. In other embodiments, the isolated antibody with B-CLL cell surface reactivity can include one or more variants of the foregoing CDRs which have 1, 2, or 3 amino acid substitutions, insertions, or deletions.

The invention further provides a pharmaceutical composition comprising an antibody of the invention and a pharmaceutically acceptable carrier.

Additionally, the invention provides a method of treating a disease or condition, such as B-CLL, which is associated with elevated levels of CD19+ B cells that are reactive with the antibody of the invention. Generally the method of treatment includes administering a therapeutically effective amount of an isolated antibody of the invention or a pharmaceutical composition thereof to a subject in need thereof.

The antibodies and compositions of the invention can also be used in diagnostic methods to detect altered levels of CD19+ B cells that are reactive with the antibody of the invention, e.g., B-CLL cells, in a sample or in a subject.

In yet another embodiment, the invention provides an isolated B-CLL cell surface marker that is reactive with the antibody of the invention.

BRIEF DESCRIPTION OF THE DRAWING(S)

FIG. 1 is a schematic diagram that depicts cell surface markers on B-CLL, including surface immunoglobulin (Ig), CD20, CD32B, and other Fcγ receptors.

FIG. 2 is a series of three histogram panels labeled A, B, and C, respectively, depicting the results (in terms of the number of events versus fluorescence intensity) of flow cytometry studies including B-CLL and goat F(ab')$_2$ anti-human IgG polyclonal antibodies conjugated to Qdot 655 nanocrystals ("gαh-Qdot") (panel A), blocked B-CLL and gαh-Qdot (panel B), or blocked B-CLL, rituximab, and gαh-Qdot (panel C).

Figure 6A:
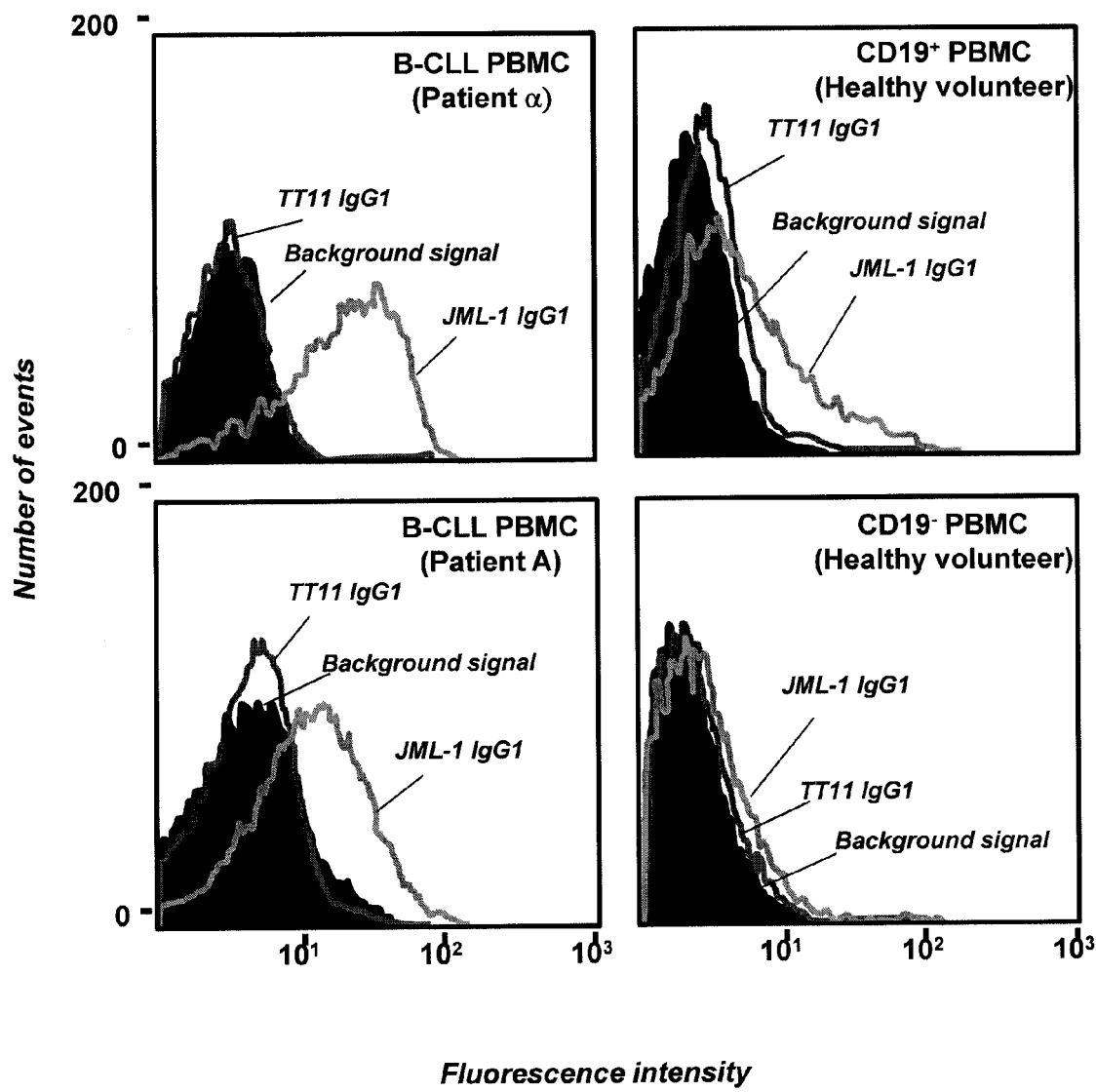

FIG. 6A is a series of four histogram panels depicting the results (in terms of the number of events versus fluorescence intensity) of flow cytometry studies testing JML-1 IgG1 reactivity to B-CLL PBMC from Patient A, JML-1 IgG1 reactivity to B-CLL PBMC from Patient α, JML-1 IgG1 reactivity to CD19+ cells from healthy volunteers, and JML-1 IgG1 reactivity to CD19– cells from healthy volunteers, respectively.

Figure 6B:
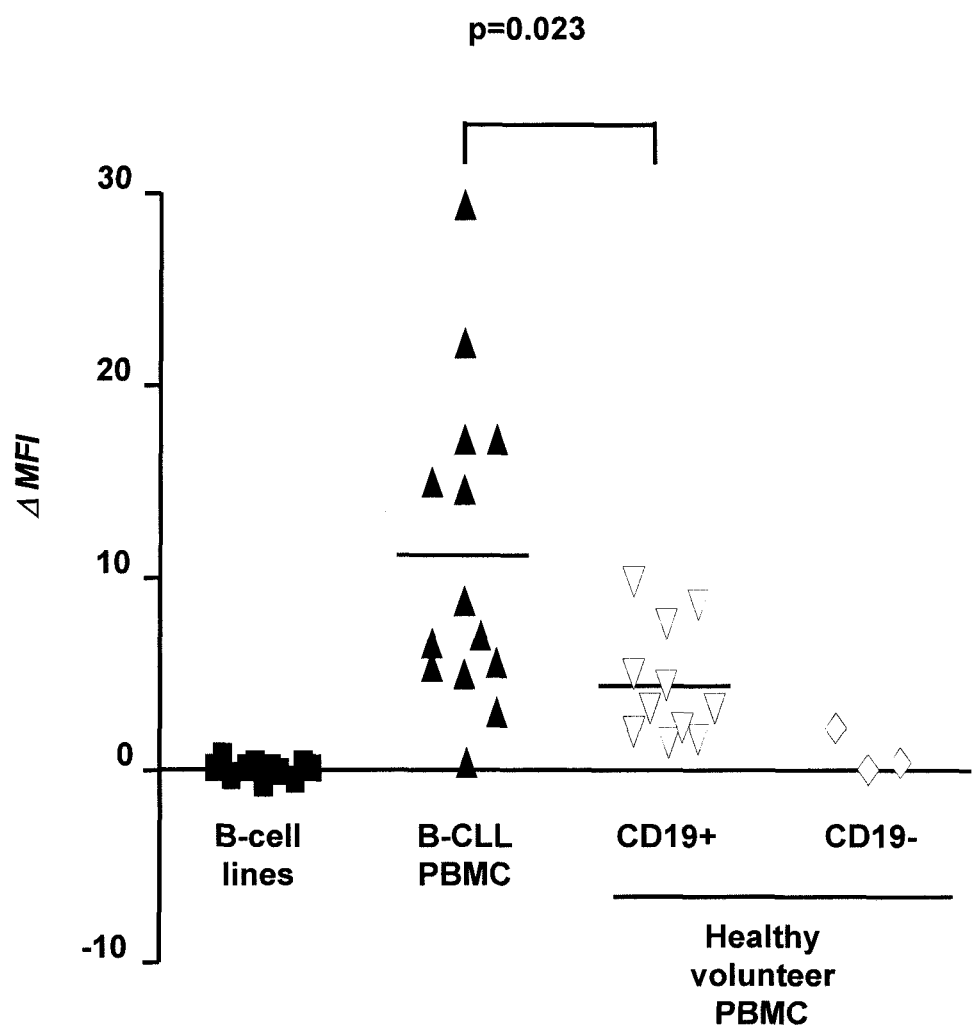

FIG. 6B is a graph depicting the results of flow cytometry

FIG. 7 is a list of the amino acid sequences corresponding to the variable region light chains (VL) of the following Fab: JML-1 (SEQ ID NO:1) including the VL framework regions (FR1-FR4) (SEQ ID NOs:2, 4, 6, and 8) and VL complementarity determining regions (CDR1-CDR3) (SEQ ID NOs:3, 5, and 7) sequences therein; JML-3 (SEQ ID NO:9) including the VL FR1-FR4 (SEQ ID NOs:10, 4, 11, and 8) and VL CDR1-CDR3 (SEQ ID NOs:3, 5, and 7) sequences therein; JML-7 (SEQ ID NO:12) including the VL FR1-FR4 (SEQ ID NOs:13, 4, 6, and 8) and VL CDR1-CDR3 (SEQ ID NOs: 3, 5, and 7) sequences therein; and JML-13 (SEQ ID NO:14) including the VL FR1-FR4 (SEQ ID NOs:15, 4, 17, and 8) and VL CDR1-CDR3 (SEQ ID NOs:3, 16, and 7) sequences therein. Underlined residues indicate a difference relative to the corresponding region in JML-1.

FIG. 8 is a list of the amino acid sequences corresponding to the variable region heavy chains (VH) of the following Fab: JML-1 (SEQ ID NO:18) including the VH FR1-FR4 (SEQ ID NOs:19, 21, 23, and 25) and VH CDR1-CDR3 (SEQ ID NOs:20, 22, and 24) sequences therein; JML-3 (SEQ ID NO:26) including the VH FR1-FR4 (SEQ ID NOs:27, 29, 23, and 25) and VH CDR1-CDR3 (SEQ ID NOs:28, 30, and 24) sequences therein; JML-7 (SEQ ID NO:31) including the VH FR1-FR4 (SEQ ID NOs:32, 29, 23, and 25) and VH CDR1-CDR3 (SEQ ID NOs:28, 30, and 24) sequences therein; and JML-13 (SEQ ID NO:33) including the VH FR1-FR4 (SEQ ID NOs:34, 29, 23, and 25) and VH CDR1-CDR3 (SEQ ID NOs:28, 30, and 24) sequences therein. Underlined residues indicate a difference relative to the corresponding region in JML-1.

DETAILED DESCRIPTION OF THE INVENTION

The invention provides an isolated antibody with specificity for a cell surface marker found on B-CLL and certain other CD19+ B cells. Thus, the antibody is said to have "reactivity" or to be "reactive" with such B cells. The invention also provides methods and compositions thereof. Additionally the invention provides the isolated B-CLL cell surface marker that is reactive with the antibody of the invention.

In particular, the invention provides an antibody having B-CLL cell surface reactivity comprising (a) a light chain variable domain having at least 90% identity to a sequence selected from the group consisting of SEQ ID NO:1, SEQ ID NO:9, SEQ ID NO:12, and SEQ ID NO:14; (b) a heavy chain variable domain having at least 90% identity to a sequence selected from the group consisting of SEQ ID NO:18, SEQ ID NO:26, SEQ ID NO:31, or SEQ ID NO:33; or (c) both a heavy chain of (a) and a light chain of (b). In a preferred embodiment, the antibody comprises both a heavy chain of (a) and a light chain of (b).

The antibody can be an isolated antibody having B-CLL cell surface reactivity comprising a light chain variable domain having at least 90% identity to a sequence selected from the group consisting of SEQ ID NO:1, SEQ ID NO:9, SEQ ID NO:12, and SEQ ID NO:14. In other embodiments, the percentage identity can be at least 91%, at least 92%, at least 93%, at least 94%, at least 95%, at least 96%, at least 97%, at least 98%, or at least 99%, or even 100%. In preferred embodiments, the light chain has at least 95% identity to a sequence selected from the group consisting of SEQ ID NO:1, SEQ ID NO:9, SEQ ID NO:12, and SEQ ID NO:14. In more preferred embodiments, the light chain has 100% identity to a sequence selected from the group consisting of SEQ ID NO:1, SEQ ID NO:9, SEQ ID NO:12, and SEQ ID NO:14.

The antibody can be an isolated antibody having B-CLL cell surface reactivity comprising a heavy chain variable domain having at least 90% identity to a sequence selected from the group consisting of SEQ ID NO:18, SEQ ID NO:26, SEQ ID NO:31, and SEQ ID NO:33. In other embodiments, the percentage identity can be at least 91%, at least 92%, at least 93%, at least 94%, at least 95%, at least 96%, at least 97%, at least 98%, or at least 99%, or even 100%. In preferred embodiments, the light chain has at least 95% identity to to a sequence selected from the group consisting of SEQ ID NO:18, SEQ ID NO:26, SEQ ID NO:31, and SEQ ID NO:33. In more preferred embodiments, the light chain has 100% identity to a sequence selected from the group consisting of SEQ ID NO:18, SEQ ID NO:26, SEQ ID NO:31, and SEQ ID NO:33.

In some embodiments, the antibody can comprise any heavy chain as described above, in combination with any suitable light chain, such as those described above. Likewise, the antibody can comprise any of the light chains as described above in combination with any suitable heavy chain, such as those described above. For example, in certain embodiments, the antibody comprises (i) a light chain variable domain with at least 90% identity to SEQ ID NO:1 and a heavy chain variable domain with at least 90% identity to SEQ ID NO:18, (ii) a light chain variable domain with at least 90% identity to SEQ ID NO:9 and a heavy chain variable domain with at least 90% identity to SEQ ID NO:26; (iii) a light chain variable domain with at least 90% identity to SEQ ID NO:12 and a heavy chain variable domain with at least 90% identity to SEQ ID NO:31; or (iv) a light chain variable domain with at least 90% identity to SEQ ID NO:14 a heavy chain variable domain with at least 90% identity to SEQ ID NO:33.

In a preferred embodiment, the antibody comprises (i) the light chain variable domain of SEQ ID NO:1 and the heavy chain variable domain of SEQ ID NO:18, (ii) the light chain variable domain of SEQ ID NO:9 and the heavy chain variable domain of SEQ ID NO:26; (iii) the light chain variable domain of SEQ ID NO:12 and the heavy chain variable domain of SEQ ID NO:31, or (iv) the light chain variable domain of SEQ ID NO:14 and the heavy chain variable domain of SEQ ID NO:33.

Percent (%) identity of peptide sequences can be calculated, for example, as $100\times(\text{identical positions})/\min(TG_A, TG_B)$, where $TG_A$ and $TG_B$ are the sum of the number of residues and internal gap positions in peptide sequences A and B in the alignment that minimizes $TG_A$ and $TG_B$. See, e.g., Russell et al., *J. Mol Biol.*, 244: 332-350 (1994).

The antibody of the invention can be any antibody including a full length antibody or an antibody fragment. The antibody can be monoclonal, recombinant, chimeric, or humanized. Preferably, the antibody contains minimal or no potentially immunogenic animal antibody-derived sequences. In a preferred embodiment, the antibody is fully human. Furthermore, the antibody can be of any isotype including without limitation IgA, IgD, IgE, IgG, or IgM. Thus, for example, the antibody can be any IgA such as IgA1 or IgA2, or any IgG such as IgG1, IgG2, IgG3, IgG4, or synthetic IgG. The antibody can also be any antibody fragment having B-CLL cell surface reactivity, such as a F(ab)2, Fv, scFv, IgGΔCH$_2$, F(ab')2, scFv2CH3, F(ab), VL, VH, scFv4, scFv3, scFv2, dsFv, Fv, scFv-Fc, (scFv)2, a bispecific antibody such as a diabody, and a bivalent antibody. The antibody can be any modified or synthetic antibody, including, but not limited to, non-depleting IgG antibodies, T-bodies, or other Fc or Fab variants of antibodies.

In addition to a heavy chain as described above, the antibody of the invention can further comprise a light chain selected from a Fab library using sequential naive chain shuffling (e.g., as described in International Patent Application Publication WO 2010/017103). Likewise, in addition to a light chain as described above, the antibody of the invention can further comprise a heavy chain selected from a Fab library using sequential naive chain shuffling.

In some embodiments, the invention provides an isolated antibody with B-CLL cell surface reactivity, comprising at least one CDR having a sequence selected from the group consisting of SEQ ID NO:3 (VL CDR1), SEQ ID NO:5 (VL CDR2), SEQ ID NO:7 (VL CDR3), SEQ ID NO:16 (VL CDR2), SEQ ID NO:20 (VH CDR1), SEQ ID NO:22 (VH CDR2), SEQ ID NO:24 (VH CDR3), SEQ ID NO:28 (VH CDR1), and SEQ ID NO:30 (VH CDR2). The invention also provides an isolated antibody with B-CLL cell surface reactivity comprising at least one or more variants of the foregoing CDR sequences, which include 1, 2, or 3 substitutions, insertions, deletions, or combinations thereof in a sequence selected from the group consisting of SEQ ID NO:3 (VL CDR1), SEQ ID NO:5 (VL CDR2), SEQ ID NO:7 (VL CDR3), SEQ ID NO:16 (VL CDR2), SEQ ID NO:20 (VH CDR1), SEQ ID NO:22 (VH CDR2), SEQ ID NO:24 (VH CDR3), SEQ ID NO:28 (VH CDR1), and SEQ ID NO:30 (VH CDR2). For example, a recombinant chimeric or fully human antibody (or fragment thereof) can include one, two, three, four, five, or six of the foregoing CDR sequences.

The antibody of the invention can be produced by any suitable technique, for example, using any suitable eukaryotic or non-eukaryotic expression system. In certain embodiments, the antibody is produced using a mammalian expression system.

The antibody of the invention can be produced using a suitable non-eukaryotic expression system such as a bacterial expression system. Bacterial expression systems can be used to produce fragments such as a F(ab)2, Fv, scFv, IgGΔCH$_2$, F(ab')2, scFv2CH3, F(ab), VL, VH, scFv4, scFv3, scFv2, dsFv, Fv, scFv-Fc, (scFv)2, and diabodies. Techniques for altering DNA coding sequences to produce such fragments are known in the art.

The antibody of the invention can be conjugated to a synthetic molecule using any type of suitable conjugation. Recombinant engineering and incorporated selenocysteine (e.g., as described in International Patent Application Publication WO 2008/122039) can be used to conjugate a synthetic molecule. Other methods of conjugation can include covalent coupling to native or engineered lysine side-chain amines or cysteine side-chain thiols. See, e.g., Wu et al., *Nat. Biotechnol.*, 23: 1137-1146 (2005). The synthetic molecule can be any molecule such as one targeting a tumor. Of course, it will be understood that the synthetic molecule also can be a protein or an antibody.

Synthetic molecules include therapeutic agents such as cytotoxic, cytostatic, or antiangiogenic agents and radioisotopes. A cytotoxic agent can be a plant, fungal, or bacterial molecule (e.g., a protein toxin). A therapeutic agent can be a maytansinoid (e.g., maytansinol or DM1 maytansinoid), a taxane, or a calicheamicin. Therapeutic agents include vincristine and prednisone. A therapeutic agent can be an antimetabolite (e.g., an antifolate such as methotrexate, a fluoropyrimidine such as 5-fluorouracil, cytosine arabinoside, or an analogue of purine or adenosine); an intercalating agent (for example, an anthracycline such as doxorubicin, daunomycin, epirubicin, idarubicin, mitomycin-C, dactinomycin, or mithramycin); a platinum derivative (e.g., cisplatin or carboplatin); an alkylating agent (e.g., nitrogen mustard, melphalan, chlorambucil, busulphan, cyclophosphamide, ifosfamide nitrosoureas, or thiotepa); an antimitotic agent (e.g., a vinca alkaloid like vincristine or taxoid such as paclitaxel or docetaxel); a topoisomerase inhibitor (for example, etoposide, and teniposide, amsacrine, or topotecan); a cell cycle inhibitor (for example, a flavopyridol); or a microbtubule agent (e.g., an epothilone, discodermolide analog, or eleutherobin analog). A therapeutic agent can be a proteosome inhibitor or a topoisomerase inhibitor such as bortezomib, amsacrine, etoposide, etoposide phosphate, teniposide, or doxorubicin. Therapeutic radioisotopes include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Antiangiogenic agents include linomide, bevacuzimab, angiostatin, and razoxane. The synthetic molecule can be another antibody such as rituximab or bevacuzimab.

A synthetic molecule can also be a label. Labels can be useful in diagnostic applications and can include, for example, contrast agents. A contrast agent can be a radioisotope label such as iodine ($^{131}$I or $^{125}$I), indium ($^{111}$In), technetium ($^{99}$Tc), phosphorus ($^{32}$P), carbon ($^{14}$C), tritium ($^{3}$H), other radioisotope (e.g., a radioactive ion), or a therapeutic radioisotope listed above. Additionally, contrast agents can include radiopaque materials, magnetic resonance imaging (MRI) agents, ultrasound imaging agents, and any other contrast agents suitable for detection by a device that images an animal body. A synthetic molecule can also be a fluorescent label, a biologically active enzyme label, a luminescent label, or a chromophore label.

In some embodiments, the antibody can also have specificity for two or more antigens on a CD19+ B-cell. For example, the antibody of the invention can be engineered (e.g., as a bivalent diabody or a conjugated Fab dimer or trimer) to have specificity for a second CD19+ B-cell surface antigen, e.g., a second cell surface antigen associated with B-CLL. In another embodiment, the antibody can be engineered to have specificity for (in addition to its B-CLL cell surface antigen) a second antigen that promotes activation or targeting of cytotoxic effector cells.

The invention further provides eukaryotic or non-eukaryotic cells that have been recombinantly engineered to produce an antibody of the invention. The eukaryotic or non-eukaryotic cells can be used as an expression system to produce the antibody of the invention. In another embodiment, the invention provides B-CLL targeted immune cells that are engineered to recombinantly express a B-CLL cell surface reactive antibody of the invention. For example, the invention provides a T-cell engineered to express an antibody of the invention (e.g., an scFv, scFv-Fc, or (scFv)2), which is linked to a synthetic molecule with the following domains: a spacer or hinge region (e.g., a CD28, CD28, or IgG hinge), a transmembrane region (e.g., a transmembrane canonical domain), and an intracellular T-cell receptor (TCR) signaling domain, thereby forming a T-body (or chimeric antigen receptor (CAR)). Intracellular TCR signaling domains that can be included in a T-body (or CAR) include, but are not limited to, CD3ξ, FcR-γ, and Syk-PTK signaling domains as well as the CD28, 4-1BB, and CD134 co-signaling domains. Methods for constructing T-cells expressing a T-body (or CAR) are known in the art. See, e.g., Marcu-Malina et al., *Expert Opinion on Biological Therapy*, 9: 539-564 (2009).

The invention provides a method of inhibiting the growth of CD19+ B cells, e.g., B-CLL, that express a cell surface antigen for an antibody of the invention. The method generally includes contacting such B cells with an antibody of the invention. The antibody can be a naked (unconjugated) antibody or an antibody conjugated to a synthetic molecule, e.g., a cytotoxic, cytostatic, or antiangiogenic agent or a radioisotope. The method can be used to inhibit the CD19+ B cells in vitro or in a subject (i.e., in vivo). The contacted B cells can be in, for example, a primary cell culture or animal model of a disorder associated with such B cells, e.g., a primary cell culture or animal model of B-CLL. The method can be used, for example, to measure and/or rank (relative to another antibody) the antibody's inhibitory activity for a specific CD19+ B cell type. Inhibiting B cells can include blocking or reducing the activity or growth of the B cells. Inhibiting can also include the killing of the CD19+ B cells. While the method is not bound by or limited to any mechanism of action, inhibitory activity can be mediated by blocking signaling of the antibody's cell surface antigen or an associated receptor. Inhibitory activity can also be mediated by recruitment of immune system effectors to attack the CD19+ B cells, e.g., by stimulating a CD8+ T-cell response, complement-dependent cytotoxicity (CDC), antibody-dependent cellular cytotoxicity (ADCC), or a combination thereof.

The invention also provides a method of treating a subject that has, is suspected to have, or is at risk for a disorder associated with CD19+ B cells expressing a cell surface antigen for an antibody of the invention. Generally, the method includes administering a therapeutically effective amount of an isolated antibody of the invention to the subject. The antibody can be any of the invention as described above. Thus, the antibody can be chimeric, humanized, synthetic, F(ab)2, Fv, scFv, IgGΔCH$_2$, F(ab')2, scFv2CH3, F(ab), VL, VH, scFv4, scFv3, scFv2, dsFv, Fv, or (scFv)2. In some embodiments, the method includes administering an IgG, an scFv, a dsFv, a F(ab')$_2$, a diabody, or a bivalent antibody. Preferably the antibody is a fully human antibody. The administered antibody can be conjugated to a synthetic molecule described above, e.g., a cytotoxic, cytostatic, or antiangiogenic agent or a therapeutic radioisotope. An exemplary cytotoxic agent is Pseudomonas exotoxin A (PE38). Disorders that can be treated include, for example, B-CLL.

The invention also provides a method of treating a subject that has, is suspected to have, or is at risk for a disorder associated with elevated levels of CD19+ B cells (e.g., B-CLL) by adoptive transfer of the genetically engineered T-cells described herein, which express an antibody of the invention as a T-body (or CAR). Recombinant technology can be used to introduce T-body (or CAR) encoding genetic material into any suitable T-cells, e.g., central memory T-cells from the subject to be treated. The T-cells carrying the genetic material can be expanded (e.g., in the presence of cytokines). The genetically engineered T-cells are transferred, typically by infusion, to the patient. The transferred T-cells of the invention can then mount an immune response against the CD19+ B cells in the subject. The adoptive transfer method can be used, for example, to treat subjects that have or are suspected to have B-CLL.

In some embodiments, the foregoing methods of treatment can further include co-administering a second therapeutic agent for the disorder associated with elevated levels of CD19+ B cells. For example, when the disorder to be treated involves B cell lymphoma or leukemia (e.g., B-CLL), the method can further include co-administration of a cytotoxic, cystostatic, or antiangiogenic agent suitable for treating the B cell cancer such as, e.g., co-administration of rituximab or alemtuzumab or utilization of a CHOP chemotherapeutic regimen.

The terms "treat," "treating," "treatment," and "therapeutically effective" used herein do not necessarily imply 100% or complete treatment. Rather, there are varying degrees of treatment, which one of ordinary skill in the art recognizes as having a potential benefit or therapeutic effect. In this respect, the inventive method can provide any amount of any level of treatment. Furthermore, the treatment provided by the inventive method can include the treatment of one or more conditions or symptoms of the disease being treated.

In another embodiment, the invention provides method of detecting in a test sample an altered level of CD19+ B cells (e.g., B-CLL cells) that are reactive with the antibody of the invention. Generally, the method includes contacting a test sample with an antibody of the invention and evaluating (e.g, determining) the amount of antibody that selectively binds to cells in the sample (e.g., by reference to a control level) to thereby qualitatively or quantitatively determine the level of CD19+ B cells (e.g., B-CLL cells) reactive with the antibody of the invention. A test sample can be from a cell culture or from a test subject, e.g., a plasma or a tissue sample from a subject that has, is suspected to have, or is at risk for a disease or condition associated with an altered level of such CD19+ B cells. A control level desirably corresponds to the amount of the antibody detected when the same antibody is contacted to a corresponding sample(s) from one or more control cultures or subjects. Methods of using the antibody of the invention to determine altered levels of CD19+ B cells can include any immunoassay such as immuno- (Western) blotting, enzyme-linked immunosorbent assay (ELISA), and flow cytometry, e.g., fluorescence-activated cell sorting (FACS) analysis.

The method of detection can be used to screen for the presence of a disorder (e.g., B-CLL) associated with an altered level of CD19+ B cells reactive with the antibody of the invention. The method includes obtaining a sample from a test subject in need of screening, e.g., a subject that has, is suspected to have, or is at risk for such a disorder. The level of reactive CD19+ B cells in the sample is measured using an antibody of the invention, and the level in the sample is compared to a control level. The control level represents, for example, the mean level (e.g., the amount or concentration) in sample(s) from one or, preferably, multiple control group subjects that do not have a disorder associated with the reactive CD19+ B cells (e.g., control group subjects that do not have B-CLL). Alternatively, the control level can correspond to the level or mean level of reactive CD19+ B cells in one or more samples taken from the test subject at one or more prior times, when the test subject did not have, or did not exhibit, a condition associated with an altered level of the reactive CD19+ B cells. A significantly altered (e.g., higher) level of the reactive CD19+ B cells in the test sample relative to the control level is indicative of a disorder associated with the reactive CD19+ B cells (e.g. B-CLL) in the subject.

Additionally, the method of detection can be used to monitor the progress of a disorder, such as B-CLL, associated with an elevated level of CD19+ B cells reactive with the antibody of the invention. The method includes obtaining a sample from a subject in need of screening, e.g., a subject having been diagnosed or suspected to have a disorder associated with an altered level of the reactive B-cells. The level of reactive B-cells in the sample is measured using an antibody of the invention, and the level in the sample is compared to a control level corresponding to the level or mean level of reactive B-cells in one or more samples taken from the test subject at one or more prior times. Levels of reactive B-cells (e.g., B-CLL) that are significantly elevated or decreased relative to the control level indicate that the subject's disorder is deteriorating or improving, respectively.

The invention provides a method for screening a subject for an altered level of CD19+ B cells that are reactive with the antibody of the invention. Generally, the method includes administering to the subject an antibody of the invention that is conjugated to a label (e.g., a contrast agent), imaging the subject in a manner suitable for detecting the label, and determining whether a region in the subject has an altered density or concentration of label as compared to the background level of label in proximal tissue. Alternatively, the method includes determining whether there is an altered density or concentration of label in a region as compared to the density or concentration of label previously detected in the same region of the subject. Methods of imaging a subject can include x-ray imaging, x-ray computed tomography (CT) imaging (e.g., CT angiography (CTA) imaging), magnetic resonance (MR) imaging, magnetic resonance angiography (MRA), nuclear medicine, ultrasound (US) imaging, optical imaging, elastography, infrared imaging, microwave imaging, and the like, as appropriate for detecting the label conjugated to the antibody. In a preferred embodiment, the subject has, is suspected to have, or is at risk for a reactive B cell tumor, such as B-CLL, and the method is used to detect the presence or absence of the tumor. In another embodiment, the method can be used to monitor the size or density of a reactive B cell tumor, such as B-CLL, over time, e.g., during a course of treatment.

The invention also provides a composition (e.g., a pharmaceutical composition) comprising an antibody as described above and a carrier (e.g., a pharmaceutically acceptable carrier). Suitable compositions, such as pharmaceutical compositions, can be prepared from any of the antibodies described herein. An exemplary composition includes a carrier and a fully human antibody having (i) the light chain variable domain of SEQ ID NO:1 and/or the heavy chain variable domain of SEQ ID NO:18, (ii) the light chain variable domain of SEQ ID NO:9 and/or the heavy chain variable domain of SEQ ID NO:26; (iii) the light chain variable domain of SEQ ID NO:12 and/or the heavy chain variable domain of SEQ ID NO:31, or (iv) the light chain variable domain of SEQ ID NO:14 and/or the heavy chain variable domain of SEQ ID NO:33. Another exemplary composition comprises a carrier and a fully human or humanized antibody having one, two, three, four, five, or six CDRs selected from the group consisting of SEQ ID NO:3 (VL CDR1), SEQ ID NO:5 (VL CDR2), SEQ ID NO:7 (VL CDR3), SEQ ID NO:16 (VL CDR2), SEQ ID NO:20 (VH CDR1), SEQ ID NO:22 (VH CDR2), SEQ ID NO:24 (VH CDR3), SEQ ID NO:28 (VH CDR1), and SEQ ID NO:30 (VH CDR2).

The composition of the invention comprises a carrier for the antibody, desirably a pharmaceutically acceptable carrier. The pharmaceutically acceptable carrier can be any suitable pharmaceutically acceptable carrier. The term "pharmaceutically acceptable carrier" as used herein means one or more compatible solid or liquid fillers, diluents, other excipients, or encapsulating substances which are suitable for administration into a human or veterinary patient (e.g., a physiologically acceptable carrier or a pharmacologically acceptable carrier). The term "carrier" denotes an organic or inorganic ingredient, natural or synthetic, with which the active ingredient is combined to facilitate the use of the active ingredient. The pharmaceutically acceptable carrier can be co-mingled with one or more of the active components, e.g., a hybrid molecule, and with each other, when more than one pharmaceutically acceptable carrier is present in the composition, in a manner so as not to substantially impair the desired pharmaceutical efficacy. "Pharmaceutically acceptable" materials typically are capable of administration to a patient without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

The pharmaceutical composition can contain suitable buffering agents, including, for example, acetic acid in a salt, citric acid in a salt, boric acid in a salt, and phosphoric acid in a salt. The pharmaceutical compositions also optionally can contain suitable preservatives, such as benzalkonium chloride, chlorobutanol, parabens, and thimerosal.

The pharmaceutical composition can be presented in unit dosage form and can be prepared by any suitable method, many of which are well known in the art of pharmacy. Such methods include the step of bringing the antibody of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, such as synthetic mono-or di-glycerides. In addition, fatty acids such as oleic acid can be used in the preparation of injectables. Carrier formulations suitable for oral, subcutaneous, intravenous, intramuscular, etc. administrations can be found in *Remington's Pharmaceutical Sciences,* Mack Publishing Co., Easton, Pa.

The delivery systems useful in the context of the invention include time-released, delayed release, and sustained release delivery systems. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The term "subject" is used herein, for example, in connection with therapeutic and diagnostic methods, to refer to human or animal subjects (e.g., mammals). Animal subjects include, but are not limited to, animal models, such as, mammalian models of conditions or disorders associated with an altered level of CD19+ B cells that are reactive with the antibody of the invention, e.g., B-CLL.

The invention also provides kits suitable for carrying out the methods of the invention. Typically, a kit comprises two or more components required for performing a therapeutic or detection method of the invention. Kit components include, but are not limited to, one or more antibodies of the invention, appropriate reagents, and/or equipment.

A kit can comprise an antibody of the invention and an immunoassay buffer suitable for detecting CD19+ B cells that are reactive with the antibody of the invention (e.g. by whole-cell ELISA or FACS). The kit may also contain one or more microtiter plates, standards, assay diluents, wash buffers, adhesive plate covers, and/or instructions for carrying out a method of the invention using the kit. The kit can include an antibody of the invention bound to a substrate (e.g., a multi-well plate or a chip), which is suitably packaged and useful to detect CD19+ B cells (e.g., B-CLL cells) that are reactive with the antibody of the invention. In some embodiments, the kit includes an antibody of the invention that is conjugated to a label, such as a fluorescent label, a biologically active enzyme label, a luminescent label, or a chromophore label. The kit can further include reagents for visualizing the conjugated antibody, e.g., a substrate for the enzyme. In some embodiments, the kit includes an antibody of the invention that is conjugated to a contrast agent and, optionally, one or more reagents or pieces of equipment useful for imaging the antibody in a subject.

Generally the antibody of the invention in a kit is suitably packaged, e.g., in a vial, pouch, ampoule, and/or any container appropriate for a therapeutic or detection method. Kit components can be provided as concentrates (including lyophilized compositions), which may be further diluted prior to use, or the kit components can be provided at the concentration intended for use. When the antibody of the invention is intended to be used in vivo, single dosages may be provided in sterilized containers having the desired amount and concentration of agents.

In another embodiment, the invention provides the isolated B-CLL cell surface marker that is reactive with the antibody of the invention. The B-CLL cell surface marker can be isolated from primary B-CLL cells using the antibody of the invention in conjunction with art-known techniques such as immunoprecipitation. The isolated B-CLL cell surface marker can be used, for example, to generate additional B-CLL cell surface reactive antibodies. Thus, the isolated B-CLL cell surface marker can be used to immunize a suitable animal (e.g., a goat, rabbit, mouse, etc.) to thereby generate polyclonal antibody with specificity for B-CLL. An antibody producing cell can be isolated from such an animal and immortalized to thereby generate monoclonal antibodies with specificity for B-CLL. Monoclonal antibodies can be further engineered to generate chimeric or fully human antibodies. Such antibodies, which are reactive with B-CLL cell surface, can be used in the methods described herein.

The isolated B-CLL cell surface marker can also be used to identify other therapeutic or diagnostic compounds (e.g., small molecule compounds, cytotoxins, etc.) that bind to the marker. Techniques for identifying such binding compounds include screening analytical microarrays or one-bead-one-compound (OBOC) libraries for immobilized compounds that bind to the isolated marker. Alternatively, the isolated B-CLL surface marker or the antibody of the invention can be immobilized on a substrate (e.g., a microarray) and used to screen compound libraries for those that inhibit the B-CLL surface marker binding to the antibody of the invention. Thus, the invention provides a method for identifying therapeutic or diagnostic compounds that includes isolating the B-CLL cell surface marker, e.g., using the antibody of the invention, and using the isolated B-CLL cell surface marker to identify a compound that binds to the marker and/or inhibits the marker from binding to the antibody of the invention.

The following examples further illustrate the invention but, of course, should not be construed as in any way limiting its scope.

EXAMPLE 1

This example demonstrates a sensitive flow cytometry assay for detecting serum antibodies with B-CLL cell surface reactivity in patients following alloHSCT.

Qdot 655 nanocrystals (Quantum Dot Corporation, Hayward, Calif.) were conjugated to goat F(ab')$_2$ anti-human IgG polyclonal antibody (gαh-Qdot) for use as a secondary antibody. Multiparameter flow cytometry was performed using an LSR II instrument (BD Biosciences, Immunocytometry Systems, San Jose, Calif.). Plasma samples from B-CLL patients and alloHSCT donors were prepared from blood and stored at −80° C. Peripheral blood mononuclear cells (PBMC) were prepared from blood using lymphocyte separation medium (MP Biomedicals, Solon, Ohio) and cryopreserved until use.

Figure 1:
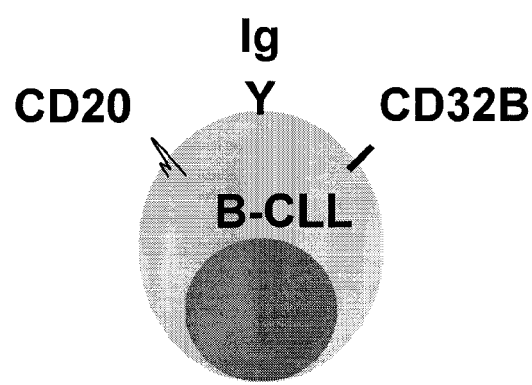
Figure 2:
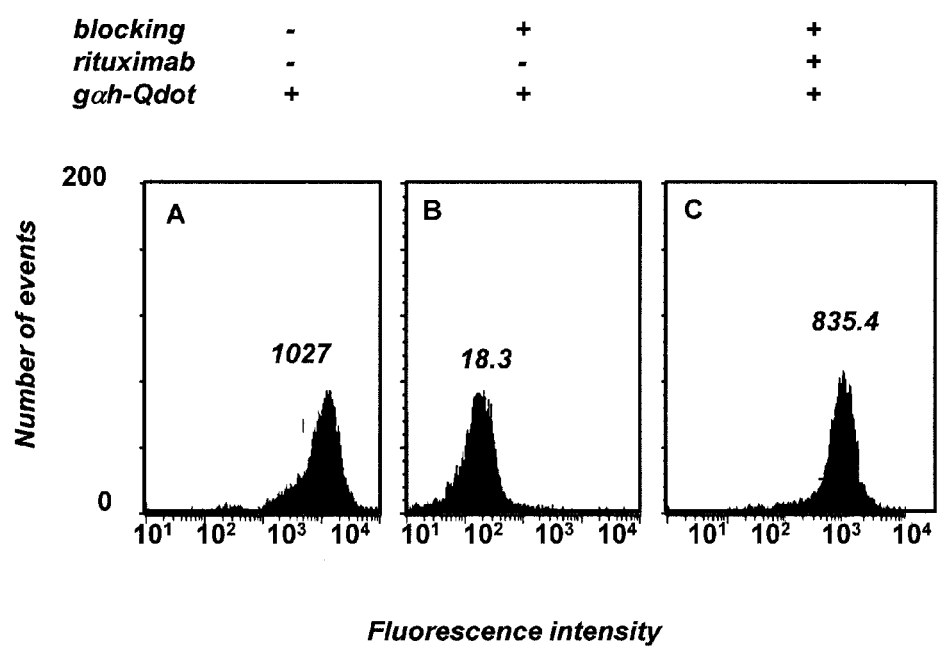

In a pilot experiment, approximately 5×10$^5$ PBMC were prepared from an untreated B-CLL patient. Detection was initially complicated by B-CLL cell surface expression of IgM, IgD, and Fcγ receptors such as CD32B, as shown in FIG. 1. The flow cytometry results are depicted in FIG. 2, panel A, which indicated that PBMC were reactive against gαh-Qdot secondary antibody alone.

To avoid gαh-Qdot detection of the human Ig displayed on B-CLL cell surface, PBMC were first blocked with 4% (v/v) normal goat serum in phosphate buffered saline (PBS) (which was also used for all subsequent dilutions and washes) followed by 100 μg/mL unconjugated goat Fab anti-human IgG polyclonal antibodies (Jackson ImmunoResearch Laboratories, West Grove, Pa.). All incubation steps were done on ice for 1 hour. After two washes, cells were incubated with 1 μg/mL rituximab (chimeric mouse/human anti-human CD20 mAb with human IgG1κ constant domains from Genentech, South San Francisco, Calif., and Biogen Idec, Cambridge, Mass.) or alemtuzumab (humanized anti-human CD52 mAb with human IgG1κ constant domains from Genzyme, Cambridge, Mass.). Following two washes, the cells were incubated with 20 nM of gαh-Qdot secondary antibody. The cells were also stained with CD3-FITC/CD19-PE or CD5-FITC/CD19-PE SIMULTEST reagents (BD Biosciences) for gating T cell and B cells, and propidium iodide for excluding dead cells from the analysis. After two more washes, a total of 20,000 gated events were collected for each sample in a list mode file, and data analysis was performed using FACS Convert and CELLQUEST software (BD Biosciences). The pilot flow cytometry assay results are depicted in FIG. 2 and demonstrate that blocking largely eliminated gαh-Qdot secondary antibody reactivity (see panel B) and allowed for specific detection of B-CLL cell surface antigens using rituximab as primary antibody (see panel C). This flow cytometry assay was similarly effective for specifically detecting alemtuzumab B-CLL antigen.

The foregoing flow cytometry assay (with blocking) was used to probe PBMC from two alloHSCT-treated B-CLL patients prior to induction chemotherapy. CD3–FITC/CD19–PE two-color SIMULTEST™ reagents were used for gating PBMC into B cells (CD3–CD19+, dominated by B-CLL cells) and T cells (CD3+CD19−). Instead of rituximab or alemtuzumab, the primary antibody used in these experiments was a 1:2 dilution of human plasma samples obtained from patients at various times before, during, and after alloHSCT. Plasma samples obtained from donors or pooled human AB serum (Invitrogen, Carlsbad, Calif.) were used as primary antibody negative controls. Characteristics of the two B-CLL patients (Patients A and B) are set forth in Table 1.

TABLE 1

|  | Patient A | Patient B |
|---|---|---|
| Indication | Relapse | Relapse |
| Sex | Male | Female |
| Age at Enrollment | 52 | 48 |
| Enrollment | 2003 | 2002 |
| National Institutes of Health Clinical Trial Web Site Identifier | NCT00055744 | NCT00003838 |
| Induction Chemotherapy | EPOCH + FR (etoposide, prednisone, cyclophosphamide, & doxorubicin) + (fludarabine, rituximab, & vincristine) | FC (fludarabine & cyclophosphamide) |
| Donor (HLA-matched, 6/6; A, B, and DR) | Brother | Brother |
| GVHD Prophylaxis | CSP + MTX (cyclosporine + methotrexate) | CSP + MTX |
| Acute GVHD | No | No |
| Chronic GVHD | No | No |
| Response | Partial response; complete response after DLI | Complete response |
| Status - May 2009 | Molecular remission | Molecular remission |

Figure 3A:
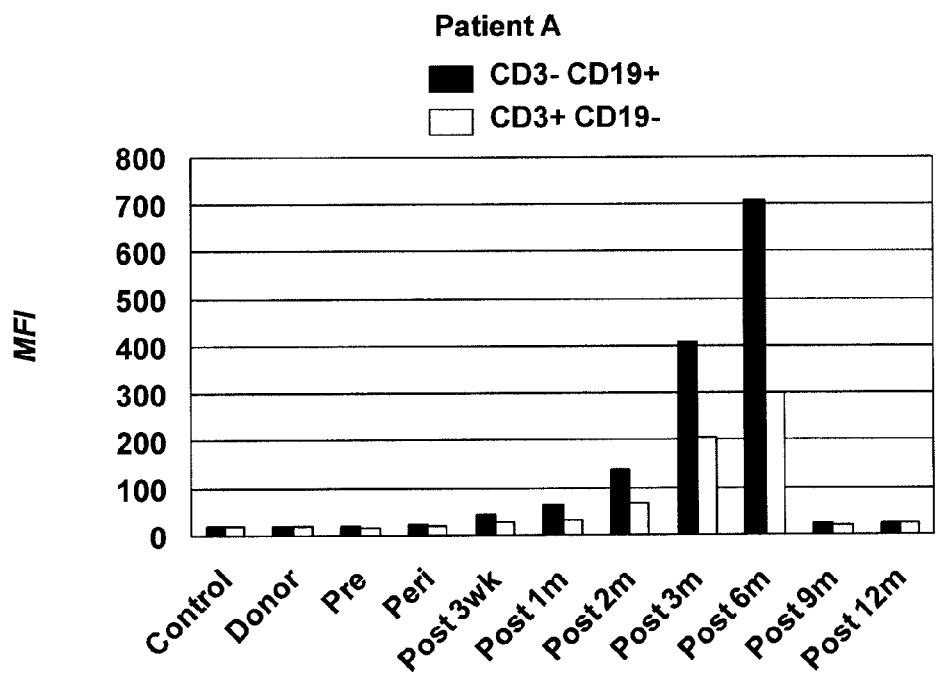
FIG. 3A is a graph depicting the results of a flow cytometry study of serum plasma reactivity to B-CLL cells (CD3−, CD19+) or T cells (CD3+, CD19−); serum plasma was obtained from Patient A at the indicated periods before (pre-), during (peri-), or after (post-) alloHSCT, and flow cytometry results are expressed in terms of mean fluorescence intensity ("MFI").
Figure 3B:
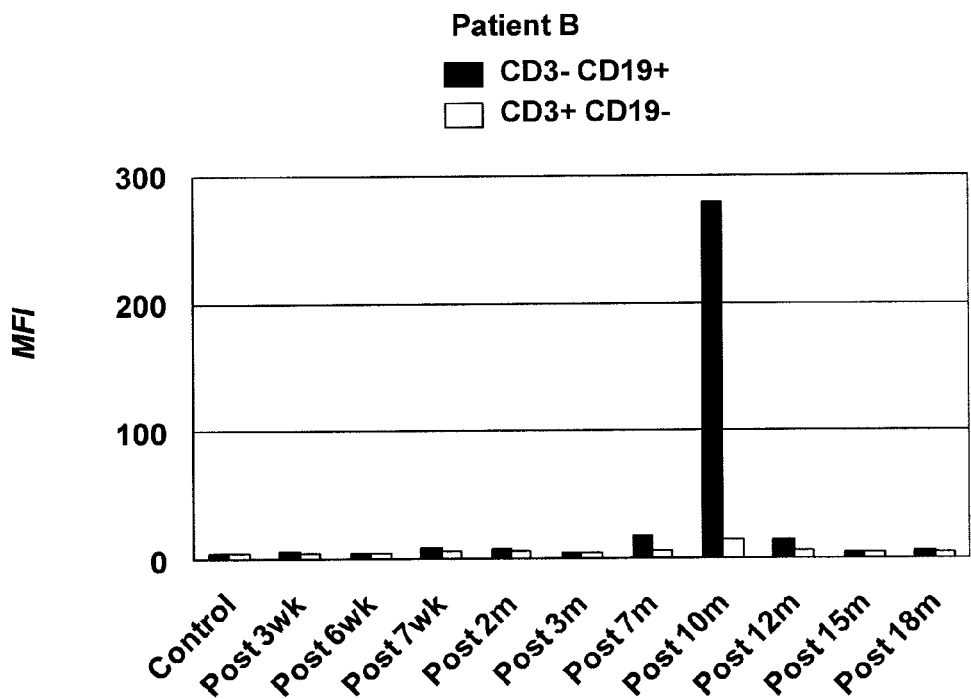
FIG. 3B is a graph depicting the results (expressed in terms of MFI) of a flow cytometry study of serum plasma reactivity to B-CLL cells (CD3−, CD19+) or T cells (CD3+, CD19−); serum plasma was obtained from Patient B at the indicated periods pre-, peri-, or post-alloHSCT.

FIGS. 3A and 3B depict flow cytometry assay results as mean fluorescence intensity ("MFI") for the B cells (black bars) and T cells (white bars) obtained from Patients A and B at the various time points before (pre), at (peri), and after (post) alloHSCT. The results shown in FIG. 3A indicate that post-alloHSCT plasma from Patient A contained substantial, though transient, B-CLL cell surface reactivity, which peaked six months after transplantation. A weaker T cell reactivity that correlated with B-CLL cell surface reactivity was also observed in Patient A (see FIG. 3A). The results in FIG. 3B show a similar pattern for Patient B, although Patient B transient B-CLL cell surface reactivity peaked at ten months after transplantation and was not accompanied by T cell surface reactivity (see FIG. 3B). By contrast, the pre- and peri-alloHSCT plasma from Patients A and B, plasma from the alloHSCT donor of Patient A, and pooled control plasma from healthy volunteers were all negative for B or T cell reactivity.

Despite the limited availability of post-alloHSCT plasma from Patients A and B at the defined time points, reactive post-alloHSCT serum antibodies were analyzed for cell surface reactivity with autologous B-CLL cells, autologous T cells, allogeneic B cells, and third party B cells using the flow cytometry assay described above. For Patient A, allogeneic B cells were derived from Patient A PBMC collected fifteen months after transplantation. For Patient B, allogeneic B cells were derived from donor PBMC. Rituximab and alemtuzumab were also analyzed for comparison. Table 2 indicates the flow cytometry results for each class of cells in terms of an MFI ratio (sample over background). An MFI ratio <2 is "−"; MFI ratio >2 and <5 is "weak", MFI ratio >5 and <20 is "+", and <100, is "++", and MFI ratio >100 is "+++". The results in Table 2 indicate some cell surface reactivity with allogeneic B cells and third party B cells. Additional analyses with secondary antibodies specific for human Ig isotypes suggested that both IgG and IgM contributed to the transient B-CLL cell surface reactivity.

TABLE 2

|  | Autologous B-CLL cells | Autologous T cells | Allogeneic B cells | Third party B cells |
|---|---|---|---|---|
| Patient A post 6 m plasma | ++ | + | − | weak |
| Patient B post 10 m plasma | ++ | weak | ++ | + |
| rituximab | ++ (Patient A) + (Patient B) | − (Patient A) − (Patient B) | ++ | ++ |
| alemtuzumab | +++ (Patient A) +++ (Patient B) | − (Patient A) − (Patient B) | +++ | +++ |

When compared to clinical data, the peak in transient B-CLL cell surface reactivity approximately paralleled the time points at which (a) full donor chimerism was achieved and (b) the disappearance of B-CLL cells by flow cytometry and PCR was noted. This suggested that the observed serum antibody response against B-CLL cells is an antigen-dependent phenomenon, likely involving both autologous and allogeneic epitopes of cell surface antigens.

The foregoing results demonstrate the successful development of an assay with sufficient sensitivity and suitability to detect serum antibodies with B-CLL cell surface reactivity in alloHSCT recipients. The foregoing data also indicate the temporal and immunological profile for these anti-B-CLL serum antibodies.

EXAMPLE 2

This example demonstrates the generation of a post-alloHSCT human Fab library.

A human Fab library was generated using cryopreserved post-alloHSCT PBMC collected from Patient A at the peak of serum antibody response, i.e., at six months after transplantation, as described in Example 1. Total RNA was extracted from $2.5 \times 10^7$ PBMC using TRI Reagent (Molecular Research Center, Cincinnati, Ohio) and further purified using the RNEASY™ Mini Kit from Qiagen (Germantown, Md.). Approximately 100 μg total RNA was isolated and validated by agarose gel electrophoresis. First-strand cDNA synthesis from total RNA using an oligo(dT) primer and SUPERSCRIPT™ reverse transcriptase (Invitrogen) was performed according to the manufacturer's protocol. $V_\kappa$, $V_\lambda$, and $V_H$ encoding sequences were separately amplified from first-strand cDNA by a 35-cycle PCR using the FastStart High Fidelity PCR System from Roche (Indianapolis, Ind.) and combinations of 12 sense/1 antisense primers for $V_\kappa$, 20 sense/3 antisense primers for $V_\lambda$, and 19 sense/6 antisense primers for $V_H$, for a total of 186 different combinations, encompassing all human germlines. The antisense primers for $V_\lambda$ and $V_H$ align to $J_\lambda$ and $J_H$ germlines, respectively, whereas the antisense primer for $V_\kappa$ aligns to the $C_\kappa$ encoding sequence. Human $C_\Lambda$-pelB and $C_\lambda$-pelB encoding sequences required for the $V_\kappa$-$C_\kappa$-$V_H$ and $V_\lambda$-$C_\lambda$-$V_H$ cassette assembly, respectively, were amplified from $pC_\kappa$ and $pC_\lambda$ as described in Hofer et al., *J. Immunol. Methods*, 318: 75-87 (2007), and Kwong et al., *J. Mol. Biol.*, 384: 1143-1156 (2008), respectively. $V_\kappa$-$C_\kappa$-$V_H$ and $V_\lambda$-$C_\lambda$-$V_H$ cassettes were assembled in one fusion step based on 3-fragment overlap extension PCR, digested with SfiI, and cloned into pC3C as also described in Kwong et al. (2008), supra. Transformation of *E. coli* strain XL1-Blue (Stratagene) by electroporation yielded $9.8\times10^7$ and $1.6\times10^8$ independent transformants for the κ and λ phagemid libraries, respectively. Randomly picked independent transformants from each library were analyzed for Fab expression by ELISA and for sequence diversity by DNA fingerprinting using AluI as described in Popkov et al., *J. Mol. Biol.*, 325: 325-335 (2003). Using VCSM13 helper phage (Stratagene), the pooled phagemid library was converted to a phage library as described Barbas et al., Phage Display: A Laboratory Manual, Cold Spring Harbor Laboratory Press (Cold Spring Harbor, N.Y., 2001). The phage library was stored at 4° C. after adding sodium azide to a final concentration of 0.02% (w/v).

Figure 4A:
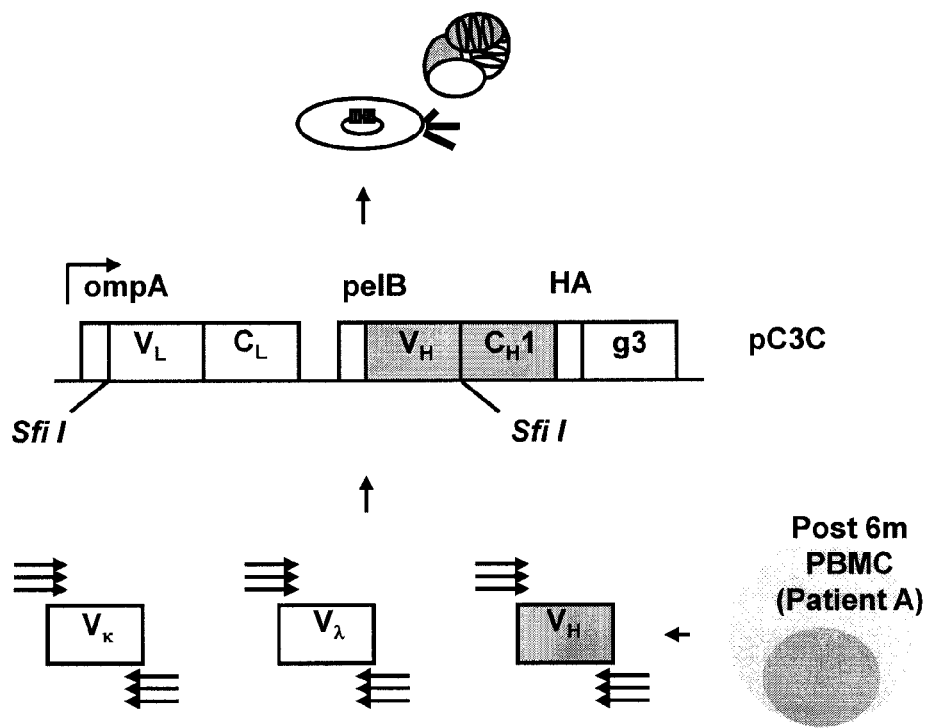
FIG. 4A is a schematic diagram depicting the strategy used to generate post-alloHSCT human Fab phage library.

FIG. 4A schematically depicts how the phage library was generated. Despite the depleted and not yet fully recovered B cell repertoire in post-alloHSCT PBMC, the post-alloHSCT PBMC phage library included $2.6\times10^8$ independent Fab clones and represented 71% for all primer combinations. This was closer than had been expected to the 89% success rate for primer combinations found in a library generated from the normal PBMC of a healthy volunteer. Table 3 sets forth the successful primer combination rate for each amplified variable region from the post-alloHSCT or normal PBMC. Phage library integrity and diversity was confirmed by ELISA and DNA fingerprinting of unselected Fab clones.

TABLE 3

|  | Post-alloHSCT PBMC | Normal PBMC |
| --- | --- | --- |
| Successful primer combinations $V_\kappa$ | 10/12 (83%) | 12/12 (100%) |
| Successful primer combinations $V_\lambda$ | 41/60 (68%) | 59/60 (98%) |
| Successful primer combinations $V_H$ | 81/114 (71%) | 95/114 (83%) |
| Total of successful primer combinations | 132/186 (71%) | 166/186 (89%) |
| Phagemid | pC3C | not applicable |
| Library size | $2.6 \times 10^8$ | not applicable |
| *E. coli* strain | XL1-Blue | not applicable |
| Helper phase | VCSM13 | not applicable |

The foregoing results demonstrate the high complexity and integrity of the post-alloHSCT human Fab library that was generated.

EXAMPLE 3

This example demonstrates the enrichment of Fab with B-CLL surface reactivity from the post-alloHSCT human Fab library.

The post-alloHSCT human Fab library was selected on cryopreserved PBMC (consisting of >85% B-CLL cells) from an untreated B-CLL patient (Patient α). The cells were maintained in 6-well tissue culture plates for 1-2 days in RPMI 1640 medium (Invitrogen) supplemented with 5% (v/v) autologous serum. Five rounds of panning were carried out using the phage display protocol described in Barbas et al., *Phage Display: A Laboratory Manual*, Cold Spring Harbor Laboratory Press (Cold Spring Harbor, N.Y., 2001), and Rader et al., *Methods Mol. Biol.*, 525: 101-128 (2009). All incubations were at room temperature unless noted otherwise. In the first round, freshly re-amplified phage library of Example 2 was pre-selected for functional Fab display through panning on rat anti-hemagglutinin (HA) mAb (Roche), which was immobilized on three wells of a 96-well ELISA plate (Costar 3690; Corning, Corning, N.Y.) at 500 ng/well. In the second round, 0.5 mL of fresh phage was first mixed with 0.5 mL of 5% (v/v) autologous serum in PBS and 0.5 mL of 1% (w/v) bovine serum albumin ("BSA") in PBS. After adding sodium azide to a final concentration of 0.12% (w/v), the phage were incubated for 30 minutes. Primary B-CLL cells from one 6-well tissue culture plate were harvested, collected through lymphocyte separation medium (MP Biomedicals), resuspended in 1.5 mL of 5% (v/v) autologous serum in PBS, counted ($4.2\times10^7$), added to the 1.5 mL phage preparation in a 15 mL polypropylene tube, and incubated for 30 minutes with gentle agitation every 5 minutes. After washing three times with 15 mL PBS, the cells were resuspended in 0.6 mL PBS containing 10 mg/mL trypsin, shaken at 37° C. and 250 rpm for 30 minutes, and added to two 2-mL XL1-Blue cultures, resuming the phage display protocol. The third round was identical to the second round, except that $1.2\times10^7$ primary B-CLL cells were used. In the fourth round, selection for functional Fab display was repeated using two wells with immobilized rat anti-HA mAb at 200 ng/well. The fifth round was identical to the second and third round, except that $5\times10^7$ primary B-CLL cells were used and four washes with 15 mL PBS were carried out.

Figure 4B:
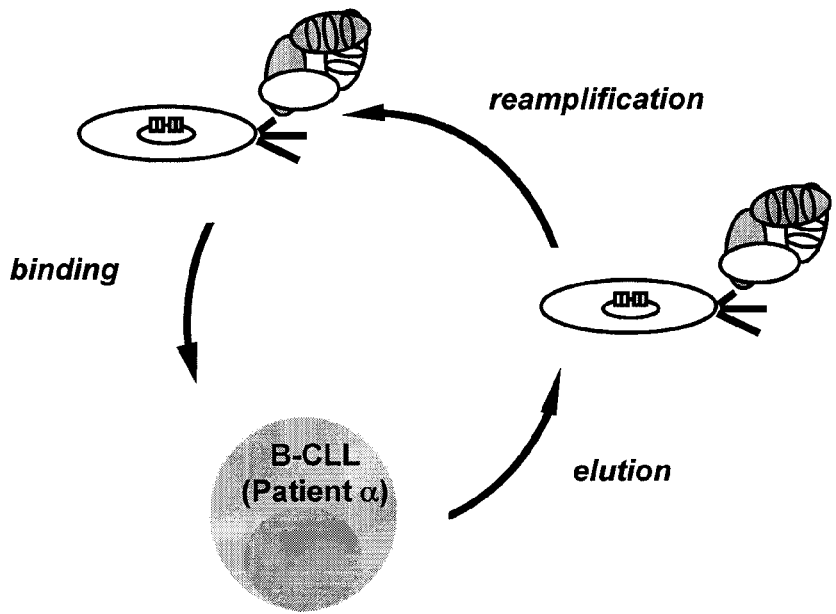
FIG. 4B is a schematic diagram depicting the enrichment of the phage library during selection rounds that included panning the library on PBMC from untreated B-CLL patient α.

In sum, the post-alloHSCT human Fab library was enriched by three selection rounds (i.e., rounds 2, 3, and 5) that included panning the library on PBMC from untreated B-CLL Patient α, as schematically depicted in FIG. 4B. Two additional rounds of panning on immobilized rat anti-HA mAb (i.e., rounds 1 and 4) were carried out prior to the first and after the second PBMC panning round to eliminate phage that did not display functional Fab with HA tag.

Figure 5A:
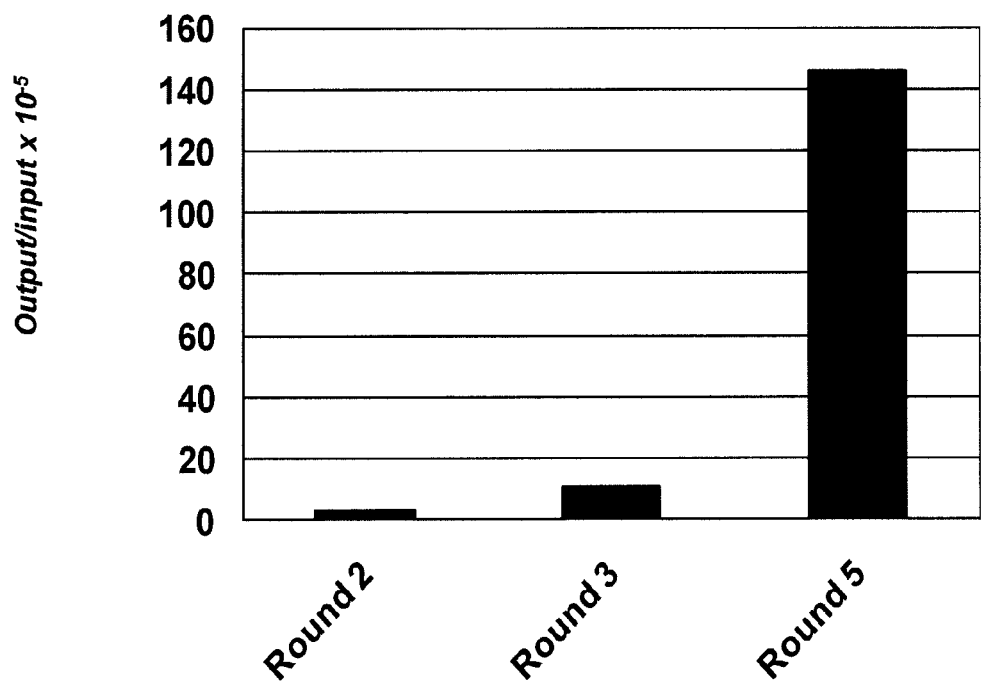
FIG. 5A is a graph depicting, for each indicated selection round, the output/input ratio of a Fab library phage.

The enrichment of phage displaying Fab with B-CLL cell surface reactivity in selection rounds 2, 3, and 5 was monitored by phage output-to-input ratio titering as described in Barbas et al. (2001) and Rader et al. (2009), supra. The phage output-to-input ratio for each selection round is depicted in FIG. 5A. The phage output-to-input ratio increased approximately 50-fold over the three cell panning selection rounds.

Figure 5B:
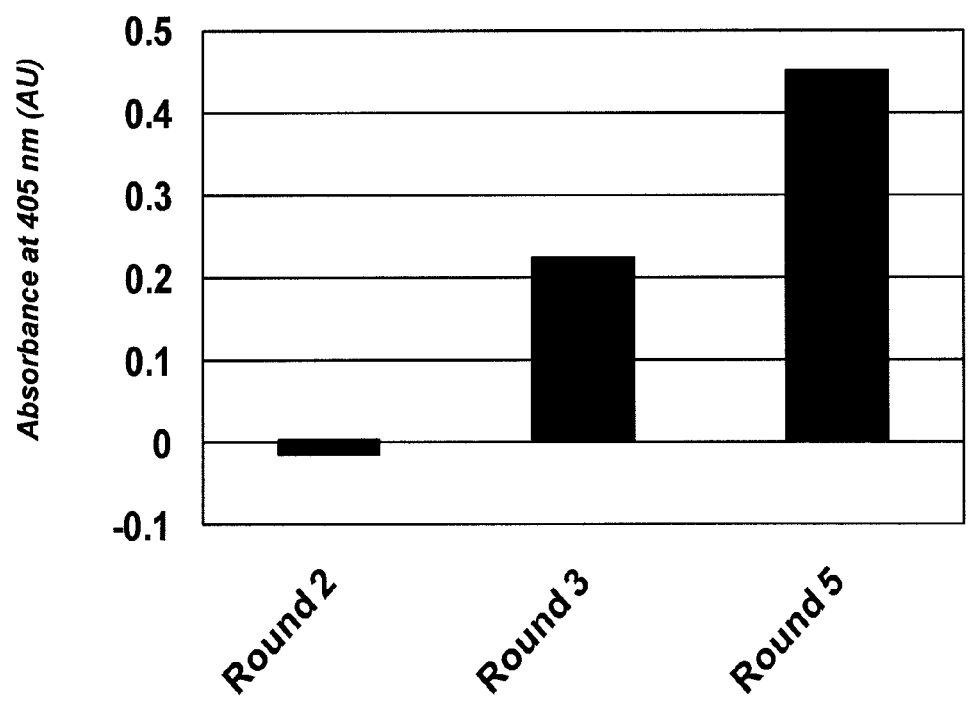
FIG. 5B is a is a graph depicting, for each indicated selection round, the results (absorbance at 405 nm) of a whole-cell ELISA study probing Fab library phage reactivity to primary B-CLL cells.

Polyclonal phage from selection rounds 2, 3, and 5 were diluted to approximately $1\times10^{11}$ phage in 75 µL PBS and stored on ice. All subsequent steps were carried out in a V-bottom 96-well tissue culture plate (Costar 3894) (Corning, Lowell, Mass.) at room temperature using PBS for washing and dilution. Approximately $5\times10^5$ primary B-CLL cells from Patient 60 were washed twice, resuspended in the 75-µL phage preparations or in PBS as a negative control, and incubated for 1 hour on a rocker. Subsequently, the cells were washed twice and incubated with 100 µL of a 1:1,000 dilution of mouse anti-phage mAb conjugated to horse radish peroxidase ("HRP") (GE Healthcare, Piscataway, N.J.) for 1 hour. The cells then were washed twice, resuspended in 50 µL HRP substrate solution, and incubated for 20 minutes. See Rader et al. (2009), supra. Absorbance at 405 nm was determined with an ELISA plate reader. The absorbance signal for each selection round was adjusted by subtracting the negative control (i.e., cells and detection antibody alone) signal. The adjusted absorbance signals for rounds 2, 3, and 5 are depicted in FIG. 5B and confirm a progressive increase of phage displaying human Fab with cell surface reactivity.

The foregoing results indicate that Fab with B-CLL surface reactivity were successfully enriched by panning against B-CLL cells from untreated Patient α.

EXAMPLE 4

This example demonstrates the identification and characterization of post-alloHSCT human Fab library clones having B-CLL surface reactivity.

One hundred selected Fab clones from the last selection round in Example 3 were analyzed for Fab expression by ELISA and for sequence diversity using AluI DNA fingerprinting as described in Popkov et al., *J. Mol. Biol.*, 325: 325-335 (2003). Of these, 85 clones were found to have Fab expression, B-CLL cell surface reactivity, and readable DNA fingerprints. Among these 85 Fab clones, 73 belonged to one of seven repeated DNA fingerprints, and 63 belonged to one of four dominating patterns with eight or more apparently identical Fab clones. Representative Fab clones, designated JML-1, -3, -7, and -13, each from one of the four dominating patterns, were further analyzed by DNA sequencing. The deduced amino acid sequences of JML-1, -3, -7, and -13 light chain and heavy chain variable domains are depicted in FIGS. 7 and 8, respectively.

The amino acid sequences of the four variable domains were analyzed with respect to germline origin, LCDR3 and HCDR3 sequences, and overall sequence identity to each other. The results of these sequence analyses are shown in Table 4. The human germline analysis, which was based on DNA alignments generated by IMGT/V-QUEST sequence analysis software (available at the INTERNATIONAL IMMUNOGENETICS INFORMATION SYSTEM web site), indicated that all four Fab clones were highly homologous with identical $V_\kappa$, $J_\kappa$, $D_H$, and $J_H$ germline origins and identical LCDR3 and HCDR3 sequences. However, all Fab clones differed by at least four amino acid mutations, and JML-1 had a different $V_H$ germline origin than JML-3, -7, and -13, despite their identical HCDR3 sequences. A BLAST search of protein databases at the National Center for Biotechnology Information web site revealed that this HCDR3 sequence, GGQTIDI, is unique among rearranged heavy chains.

As indicated in Table 4, JML-3, -7, and -13 included approximately 2% overall deviation from their $V_\kappa$ and $V_H$ germline sequences. JML-1deviated approximately 7% from its $V_H$ germline sequence (see Table 4). This deviation is evidence of somatic hypermutation in the heavy chain of JML-1.

Four to five selected clones with identical fingerprints corresponding to JML-1, -3, -7, or -13 were selected, and Fab expression was induced with isopropyl β-D-1-thiogalactopyranoside as described in Rader et al. (2009), supra. Supernatants were pooled and concentrated ten-fold using a 15 mL Amicon Ultra Centrifugal Filter Device with 10-kDa molecular weight cut off (Millipore, Billerica, Mass.) to generate crude Fab samples corresponding to JML-1, -3, -7, and -13. Crude Fab samples (75 μL) were analyzed by whole-cell ELISA, as described in Example 3, using PBMC from untreated B-CLL Patient α. Crude Fab samples prepared from pooled clones with the JML-1 fingerprint consistently revealed the strongest B-CLL cell surface reactivity.

The foregoing results demonstrates the preparation of four exemplary Fab antibodies of the invention. The high homologies among JML-1, -3, -7, and -13 Fab, in particular their identical LCDR3 and HCDR3 sequences, imply that these four exemplary Fab antibodies recognize the same antigen. However, their primary usefulness is based on B-CLL cell surface reactivity and does not require that they recognize the same surface antigen.

EXAMPLE 5

This example demonstrates the generation, expression, purification, and biotinylation of JML-1 IgG 1.

JML-1 $V_H$ and light chain encoding sequences were PCR amplified using appropriately designed primers and cloned into mammalian expression vector PIGG as previously described in Hofer et al., *J. Immunol. Methods*, 318: 75-87 (2007) and Rader et al., *FASEB J.*, 16: 2000-2002 (2002). 300 μg of the resulting PIGG-JML-1 plasmid in 293FECTIN transfection reagent (Invitrogen) was transiently transfected into 3×10⁸ HEK 293F cells. Transfected cells were maintained in 300 mL FreeStyle serum-free medium in a 500-mL spinner flask on a stirring platform at 75 rpm (CELLSPIN System; Integra Biosciences, Chur, Switzerland) in a humidified atmosphere containing 8% $CO_2$ at 37° C. After four days,

TABLE 4

|  | JML-1 | JML-3 | JML-7 | JML-13 |
|---|---|---|---|---|
| Light chain |  |  |  |  |
| Human germlines | $V_\kappa$ 1-39 | $V_\kappa$ 1-39 | $V_\kappa$ 1-39 | $V_\kappa$ 1-39 |
|  | $J_\kappa$ 3 | $J_\kappa$ 3 | $J_\kappa$ 3 | $J_\kappa$ 3 |
| Deviation from $V_\kappa$ germline | 0/95 | 2/95 | 1/95 | 3/95 |
| LCDR3 sequence | QQSYSTPFT | QQSYSTPFT | QQSYSTPFT | QQSYSTPFT |
|  | (SEQ ID NO: 7) | (SEQ ID NO: 7) | (SEQ ID NO: 7) | (SEQ ID NO: 7) |
| Sequence identity to JML-1 | 100% | 98% | 99% | 97% |
| Sequence identity to JML-3 | 98% | 100% | 97% | 95% |
| Sequence identity to JML-7 | 99% | 97% | 100% | 96% |
| Sequence identity to JML-13 | 97% | 95% | 96% | 100% |
| Heavy chain |  |  |  |  |
| Human germlines | $V_H$ 3-9 | $V_H$ 3-30 | $V_H$ 3-30 | $V_H$ 3-30 |
|  | $D_H$ 3-10 | $D_H$ 3-10 | $D_H$ 3-10 | $D_H$ 3-10 |
|  | $J_H$ 3 | $J_H$ 3 | $J_H$ 3 | $J_H$ 3 |
| Deviation from $V_H$ germline | 7/98 | 2/98 | 2/98 | 1/98 |
| HCDR3 sequence | GGQTIDI | GGQTIDI | GGQTIDI | GGQTIDI |
|  | (SEQ ID NO: 24) | (SEQ ID NO: 24) | (SEQ ID NO: 24) | (SEQ ID NO: 24) |
| Sequence identity to JML-1 | 100% | 89% | 90% | 88% |
| Sequence identity to JML-3 | 89% | 100% | 99% | 99% |
| Sequence identity to JML-7 | 90% | 99% | 100% | 98% |
| Sequence identity to JML-13 | 88% | 99% | 98% | 100% | the medium was collected after centrifugation, replaced for additional three to four days, and collected again. Pooled supernatants were then processed, and IgG1 was purified using a 1 mL recombinant Protein A HITRAP column (GE Healthcare) as previously described in Hofer et al. (2007), supra. The quality and quantity of purified IgG1 was determined by SDS-PAGE and $A_{280}$ absorbance. In parallel with JML-1, the previously described human anti-tetanus toxoid mAb TT11 IgG1 was expressed and purified as a negative control. See Kwong et al., *J. Mol. Biol.*, 384: 1143-1156 (2008). Purified JML-1 IgG1 and TT11 IgG1 were biotinylated using the BiotinTag Micro-Biotinylation Kit (Sigma-Aldrich, St. Louis, Mo.). The number of conjugated biotin molecules per IgG1 molecule was approximately four for each of JML-1 and TT11 IgG1.

The flow cytometry assay described in Example 1 was used to confirm that JML-1 IgG1, but not TT11 IgG1, strongly bound to B-CLL cells from Patient α (who was used for library selection). JML-1 IgG1 also recognized B-CLL cells from Patient A (the alloHSCT recipient from whom the library had been generated). The results of the foregoing flow cytometry assays are depicted in the histograms labeled Patient α and Patient A, respectively, in FIG. 6A.

To characterize JML-1 IgG, PBMC were prepared from 12 B-CLL patients that were not involved in generating and selecting the Fab library. PBMC were also prepared from the freshly drawn blood of healthy volunteers, and the CD19+ and CD19− subpopulations were purified by magnetic activated cell sorting (MACS) using CD19 MicroBeads (Miltenyi Biotec, Auburn, Calif.). Additionally JML-1 IgG was characterized for its ability to bind the following eleven cell lines. Five cell lines were generated using Epstein-Barr virus (EBV) to transforin B lymphoblastoid cell lines (EBV-LCL) obtained from PBMC of healthy volunteers (583, 0745, and 1363) and B-CLL patients (18-7-3 and 18-1-12) as previously described. Aman et al., J. Exp. Med., 159: 208-220 (1984). PCR amplification of Ig heavy chain VDJ gene fragments from genomic DNA indicated that EBV-LCL 0745 was polyclonal and that EBV-LCL 18-7-3 and 18-1-12 were monoclonal, albeit different in HCDR3 lengths than the corresponding B-CLL cells (suggesting EBV transformation of normal B cells present in these B-CLL patients). The B-CLL cell line EHEB was obtained from the German Collection of Microorganisms and Cell Cultures (Braunschweig, Germany). Saltman et al., *Leuk. Res.,* 14: 381-387 (1990). The B-CLL cell line 232-B4 was kindly provided by Dr. Anders Rosen (Linkoping University, Linköping, Sweden). Wendel-Hansen et al., *Leukemia,* 8: 476-484 (1994). Human Burkitt's lymphoma B-cell lines Daudi, Raji, and Ramos and human mantle cell lymphoma B-cell line JeKo-1 were obtained from American Type Culture Collection (Manassas, Va.).

Approximately $5 \times 10^5$ cells (from the PBMC of a B-CLL patient, from MACS-separated PBMC of a healthy volunteer, or from a cell line) were blocked with pooled human AB serum. All incubation steps were done on ice for 1 hour. The cells were incubated with 10 μg/mL biotinylated JML-1 or biotinylated TT11 IgG1 in 2% (v/v) fetal bovine serum (FBS) (Hyclone, Logan, Utah) in PBS (which was used for all subsequent dilutions and washes), followed by two washes, incubation with 2 μg/mL PE-coupled streptavidin (BD Biosciences), and two more washes. Propidium iodide was added to exclude dead cells from the analysis. Flow cytometry was performed using a FACSCALIBUR™ instrument (BD Biosciences) and analyzed with CELLQUEST™ software. The flow cytometry assay results for each of the foregoing cell sources are depicted as mean fluorescence intensity ("MFI") in FIG. 5B.

As shown in FIG. 5B, JML-1 IgG1 but not TT11 IgG1 was reactive to B-CLL in 11 of the 12 B-CLL patients that were not involved in generating or selecting the Fab library. These results indicate that the antigen recognized by JML-1 is broadly expressed in B-CLL and is not restricted to Patients A and α.

Some variability of JML-1 IgG1 reactivity was found among the cells derived from different B-CLL patients and in the CD19+ subpopulation of PBMC derived from different healthy volunteers (but not in the corresponding CD19− subpopulations), as depicted in FIGS. 5A and 5B. Nonetheless, compared to primary B cells, the mean JML-1 IgG1 reactivity measured for primary B-CLL cells was significantly higher (p=0.023) as indicated in FIG. 5B. None of the eleven human B-cell lines analyzed revealed significant JML-1 IgG1 reactivity (see FIG. 5B). Collectively, these findings suggested that the antigen recognized by JML-1 IgG is restricted to primary B cells and over-expressed in primary B-CLL cells.

The foregoing results demonstrate the preparation of an IgG antibody of the invention and its usefulness for detecting B-CLL and other CD19+ B cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated antibody having B-cell chronic lymphocytic leukemia (B-CLL) cell surface reactivity, comprising:
   (i) the light chain variable domain sequence of SEQ ID NO:1 and the heavy chain variable domain sequence of SEQ ID NO:18;
   (ii) the light chain variable domain sequence of SEQ ID NO:9 and the heavy chain variable domain sequence of SEQ ID NO:26;
   (iii) the light chain variable domain sequence SEQ ID NO:12 and the heavy chain variable domain sequence of SEQ ID NO:31; or
   (iv) the light chain variable domain sequence of SEQ ID NO:14 and the heavy chain variable domain sequence of SEQ ID NO:33.

2. An isolated antibody with B-CLL cell surface reactivity, comprising the following complementarity determining regions (CDRs):
   (i) SEQ ID NO:3 as CDRL1, SEQ ID NO:5 as CDRL2, SEQ ID NO:7 as CDRL3, SEQ ID NO:20 as CDRH1, SEQ ID NO:22 as CDRH2, and SEQ ID NO:24 as CDRH3;
   (ii) SEQ ID NO:3 as CDRL1, SEQ ID NO:5 as CDRL2, SEQ ID NO:7 as CDRL3, SEQ ID NO:28 as CDRH1, SEQ ID NO:30 as CDRH2, and SEQ ID NO:24 as CDRH3; or
   (iii) SEQ ID NO:3 as CDRL1, SEQ ID NO:16 as CDRL2, SEQ ID NO:7 as CDRL3, SEQ ID NO:28 as CDRH1, SEQ ID NO:30 as CDRH2, and SEQ ID NO:24 as CDRH3.

3. The antibody of claim 2, wherein the antibody includes SEQ ID NO:23 as VH framework region 3, SEQ ID NO:24 as CDRH3, AND SEQ ID NO:25 as VH framework region 4.

4. The antibody of claim 2, wherein the antibody includes SEQ ID NO:3 as CDRL1, SEQ ID NO:4 as VL framework region 2, SEQ ID NO:7 as CDRL3, and SEQ ID NO:8 as VL framework region 4.

5. The antibody of claim 2, wherein the antibody is selected from the group consisting of IgA1, IgA2, IgD, IgE, IgG1, IgG2, IgG3, IgG4, IgM, F(ab)2, Fv, scFv, IgGΔCH$_2$, F(ab')2, Fab, dsFv, Fv, scFv-Fc, a non-depleting IgG, a diabody, a T-body, a bispecific antibody, and a bivalent antibody.

6. The antibody of claim 5, wherein the antibody is an IgG selected from the group consisting of IgG1, IgG2, IgG3, IgG4, and synthetic IgG.

7. The antibody of claim 5, wherein the antibody is a Fab.

8. The antibody of claim 5, wherein the antibody is a dsFv.

9. The antibody of claim 2, wherein the antibody is conjugated to a synthetic molecule.

10. The antibody of claim 9, wherein the antibody is a T-body, and the synthetic molecule comprises a transmembrane region and an intracellular T-cell receptor (TCR) signaling domain.

11. The antibody of claim 9, wherein the synthetic molecule is a label.

12. The antibody of claim 9, wherein the synthetic molecule is a cytotoxic agent or a therapeutic radioisotope.

13. The antibody of claim 2, wherein the antibody is a fully human antibody.

14. A pharmaceutical composition comprising a therapeutically effective amount of an isolated antibody of claim 2 and a pharmaceutically acceptable carrier.

15. A kit comprising the isolated antibody of claim 2.

16. The kit of claim 15, further comprising one or more immunoassay buffers.

17. The kit of claim 15, wherein the antibody is conjugated to a label.

* * * * *